(12) United States Patent
Fernandez et al.

(10) Patent No.: US 9,074,045 B2
(45) Date of Patent: Jul. 7, 2015

(54) PROCESS FOR THE MANUFACTURE OF POLYCARBONATE COMPOSITIONS

(71) Applicant: SABIC Innovative Plastics IP B.V., Bergen op Zoom (NL)

(72) Inventors: Ignacio Vic Fernandez, Santo Angel (ES); Isabel Macian Aviles, Cartagena (ES)

(73) Assignee: SABIC GLOBAL TECHNOLOGIES B.V. (NL)

( * ) Notice: Subject to any disclaimer, the term of this patent is extended or adjusted under 35 U.S.C. 154(b) by 0 days.

(21) Appl. No.: 14/308,866

(22) Filed: Jun. 19, 2014

(65) Prior Publication Data
US 2014/0378643 A1    Dec. 25, 2014

(30) Foreign Application Priority Data
Jun. 20, 2013   (EP) ..................... 13382234

(51) Int. Cl.
| | |
|---|---|
| *C08G 64/00* | (2006.01) |
| *C08G 64/30* | (2006.01) |
| *C08G 64/06* | (2006.01) |
| *G01N 29/024* | (2006.01) |
| *G01N 29/44* | (2006.01) |
| *B01J 19/00* | (2006.01) |
| *B01J 19/18* | (2006.01) |
| *B01J 19/24* | (2006.01) |
| *C08G 63/02* | (2006.01) |

(52) U.S. Cl.
CPC .............. *C08G 64/307* (2013.01); *C08G 64/06* (2013.01); *G01N 29/024* (2013.01); *G01N 29/44* (2013.01); *G01N 2291/02809* (2013.01); *G01N 2291/024* (2013.01); *B01J 2219/00186* (2013.01); *B01J 19/0006* (2013.01); *B01J 19/1862* (2013.01); *B01J 19/242* (2013.01); *B01J 2219/00067* (2013.01); *B01J 2219/00069* (2013.01); *B01J 2219/00094* (2013.01); *B01J 2219/00164* (2013.01); *B01J 2219/00182* (2013.01); *B01J 2219/002* (2013.01); *B01J 2219/00209* (2013.01); *B01J 2219/00213* (2013.01); *B01J 2219/00231* (2013.01)

(58) Field of Classification Search
USPC .................................. 528/196, 198
See application file for complete search history.

(56) References Cited

U.S. PATENT DOCUMENTS

| | | |
|---|---|---|
| 2003/0032725 A1 | 2/2003 | Gaggar et al. |
| 2003/0199665 A1 | 10/2003 | Kimura et al. |
| 2007/0197764 A1 | 8/2007 | Yokota et al. |

OTHER PUBLICATIONS

DE10347826 Machine Translation; Date of Publication May 12, 2005; 21 pages.
European Search Report for European Application No. 13382234.6; Date of Completion: Aug. 1, 2013; 5 pages.

*Primary Examiner* — Terressa Boykin
(74) *Attorney, Agent, or Firm* — Cantor Colburn LLP

(57) ABSTRACT

A continuous process for the manufacture of a polycarbonate comprises: combining an aromatic dihydroxy compound stream and a diaryl carbonate stream to form a mixture; controlling a weight or molar ratio of the diaryl carbonate to the aromatic dihydroxy compound by: measuring a sound velocity, Vs, in the mixture at an operating temperature of the controlling step; and determining the weight or molar ratio of the diaryl carbonate to the aromatic dihydroxy compound in the mixture; and adjusting a flow rate of at least one of the aromatic dihydroxy compound stream and the diaryl carbonate stream, if needed, to achieve a desired weight or molar ratio of the diaryl carbonate to the aromatic dihydroxy compound; and polymerizing the aromatic dihydroxy compound and the diaryl carbonate in the presence of a catalyst to produce the polycarbonate.

19 Claims, 7 Drawing Sheets

PROCESS FOR THE MANUFACTURE OF POLYCARBONATE COMPOSITIONS

CROSS-REFERENCE TO RELATED APPLICATION

This application claims the benefit of European Patent Application Serial No. 13382234.6 filed Jun. 20, 2013. The related application is incorporated herein by reference.

TECHNICAL FIELD

This disclosure relates to a process for the manufacture of polycarbonate compositions; more specifically, to a continuous melt process for the manufacture of polycarbonate compositions from monomers having controlled molar ratios.

BACKGROUND

Polycarbonate is widely used as a raw material in many different manufacturing sectors. It is believed that the demand for polycarbonate will increase significantly in the coming years and as such, improvements in the polymerization process are currently being developed.

Several processes for the production of polycarbonate are known, for example through the reaction of an aromatic dihydroxy compound and diaryl carbonate.

The aromatic dihydroxy compound and the diaryl carbonate are generally added in a molar ratio of 1:1 based on stoichiometric considerations, where at later stages in the polymerization, additional diaryl carbonate can be added to, for example, compensate for losses along the polymer process or to increase the endcap level in the final polycarbonate.

The relative amounts of both the aromatic dihydroxy compound and diaryl carbonate are generally controlled typically using mass flow meters, but even with this type of instrumentation, it is often found that significant deviations in the formulated monomer molar ratio exist. These deviations can alter the value of the endcap ratio in the final product and can therefore affect such properties as the heat aging stability of the polycarbonate.

Due to the increasing demands on polycarbonate production, the process for production of polycarbonate leaves ample room for improvement, in particular in view of the way the raw materials are introduced.

BRIEF DESCRIPTION

A process for monitoring a relative level of an aromatic dihydroxy compound or a diaryl carbonate in a mixture comprising the aromatic dihydroxy compound and the diaryl carbonate, comprises: measuring a sound velocity, Vs, in the mixture at an operating temperature of the process; and determining the relative level of the aromatic dihydroxy compound or the diaryl carbonate in the mixture based on Equation 1, 2, 3 or 4:

$$WP1 = a + b \times Vs \quad \text{(Equation 1)}$$

$$WP2 = 100 - (a + b \times Vs) \quad \text{(Equation 2)}$$

$$WR = [100 - (a + b \times Vs)]/(a + b \times Vs) \quad \text{(Equation 3)}$$

$$MR = (Mw1/Mw2) \times [100 - (a + b \times Vs)]/(a + b \times Vs) \quad \text{(Equation 4)}$$

wherein WP1 is the weight percent of the aromatic dihydroxy compound in the mixture, WP2 is the weight percent of the diaryl carbonate in the mixture, Mw1 is the molecular weight of the aromatic dihydroxy compound, Mw2 is the molecular weight of the diaryl carbonate, WR is the weight ratio of the diaryl carbonate to the aromatic dihydroxy compound, MR is the molar ratio of the diaryl carbonate to the aromatic dihydroxy compound, and a and b are constants.

A continuous process for the manufacture of a polycarbonate comprises: combining an aromatic dihydroxy compound stream and a diaryl carbonate stream to form a mixture; controlling a weight or molar ratio of the diaryl carbonate to the aromatic dihydroxy compound by: measuring a sound velocity, Vs, in the mixture at an operating temperature of the controlling step; and determining the weight or molar ratio of the diaryl carbonate to the aromatic dihydroxy compound in the mixture based on Equation 3 or Equation 4:

$$WR = [100 - (a + b \times Vs)]/(a + b \times Vs) \quad \text{(Equation 3)}$$

$$MR = (Mw1/Mw2) \times [100 - (a + b \times Vs)]/(a + b \times Vs) \quad \text{(Equation 4)}$$

wherein Mw1 is the molecular weight of the aromatic dihydroxy compound, Mw2 is the molecular weight of the diaryl carbonate, WR is the weight ratio of the diaryl carbonate to the aromatic dihydroxy compound, MR is the molar ratio of the diaryl carbonate to the aromatic dihydroxy compound, and a and b are constants; and adjusting a flow rate of at least one of the aromatic dihydroxy compound stream and the diaryl carbonate stream, if needed, to achieve a desired weight or molar ratio of the diaryl carbonate to the aromatic dihydroxy compound; and polymerizing the aromatic dihydroxy compound and the diaryl carbonate in the presence of a catalyst to produce the polycarbonate.

BRIEF DESCRIPTION OF THE DRAWINGS

Refer now to the drawings, which are exemplary, not limiting, and wherein like elements are numbered alike in several figures.

DETAILED DESCRIPTION

Figure 5A:
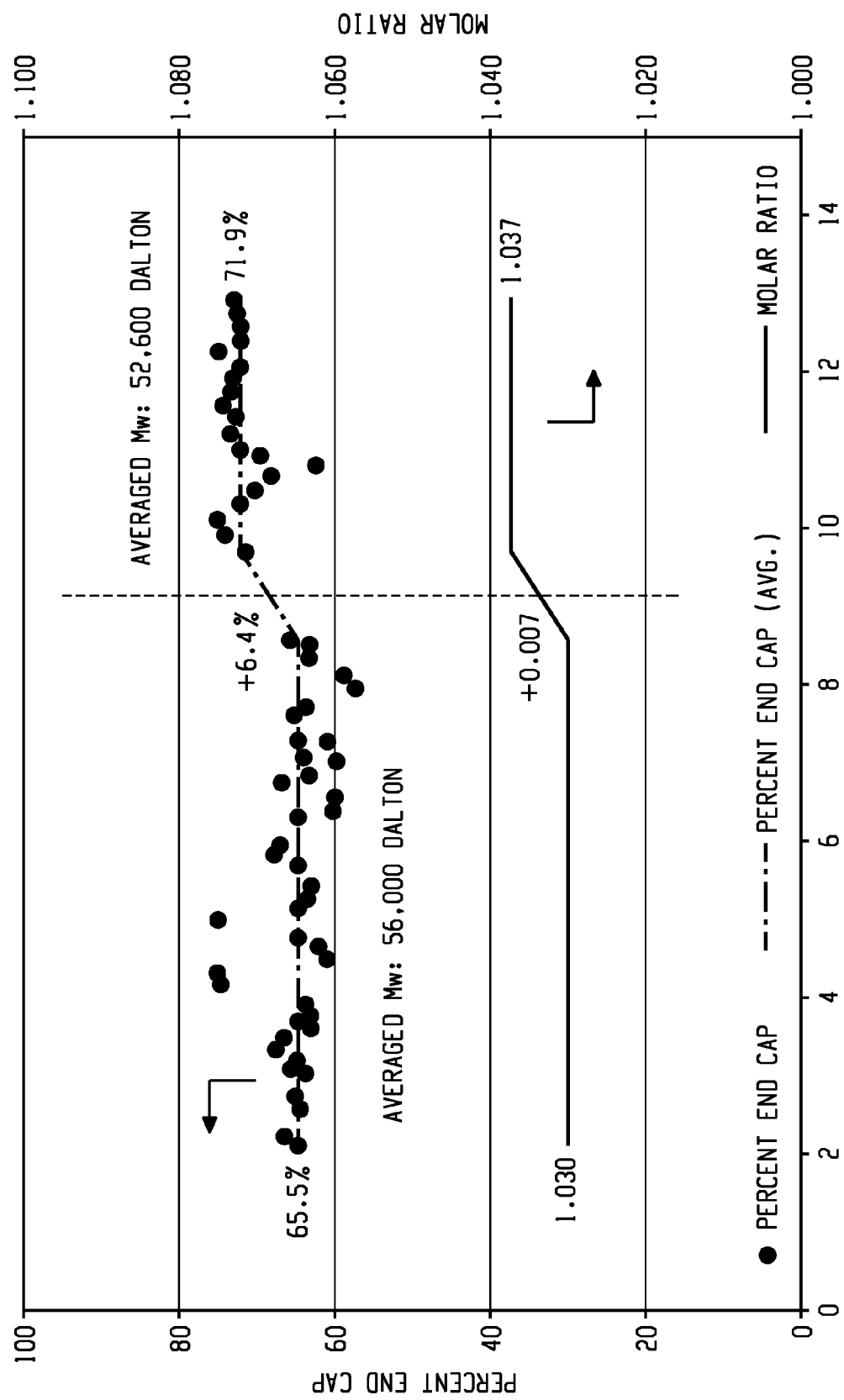
FIGS. 5a and 5b illustrate the effect of a change in DPC/BPA molar ratio in the pre-mixer on the endcap ratio in the polycarbonate product.
Figure 5B:
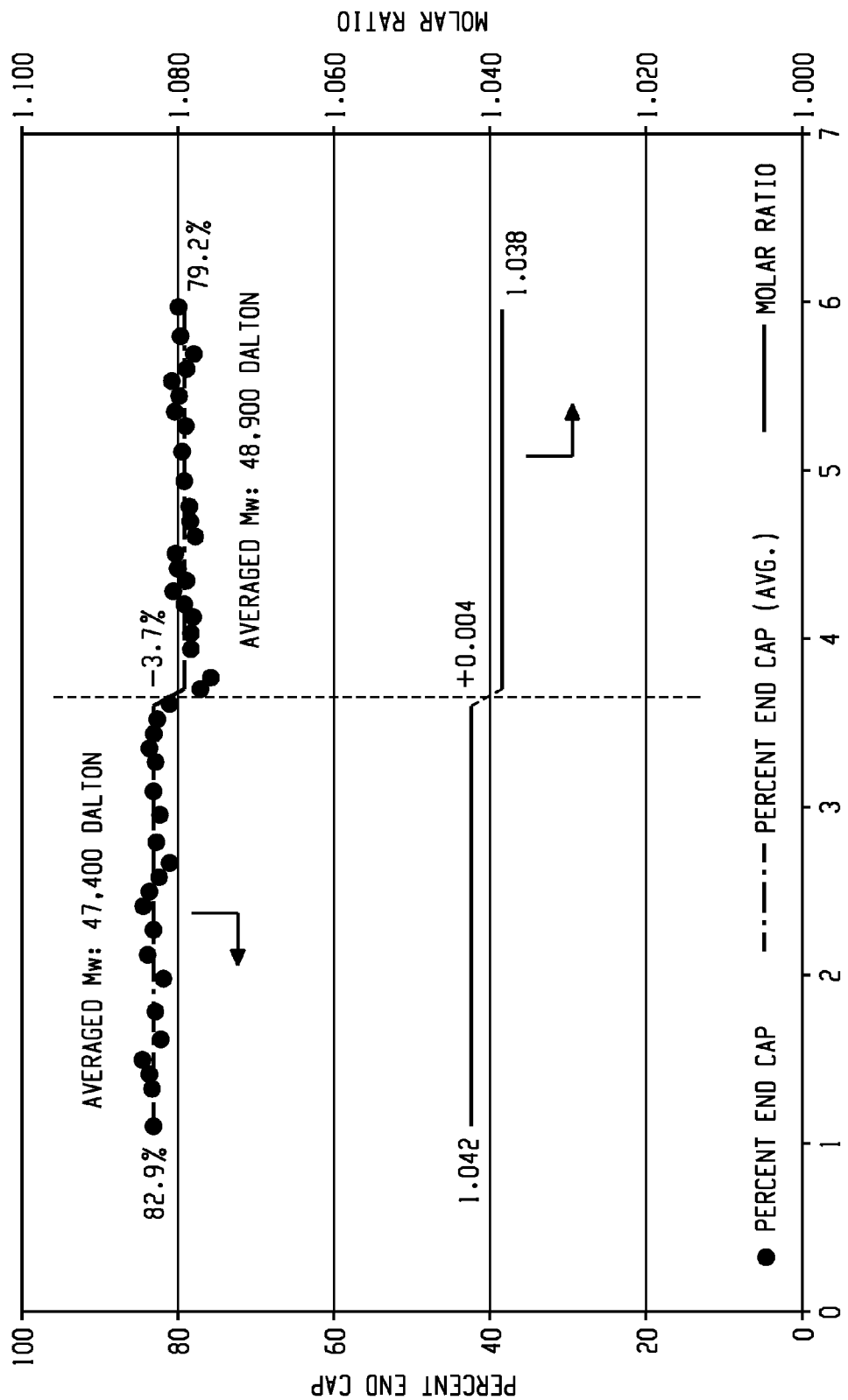
Figure 6:
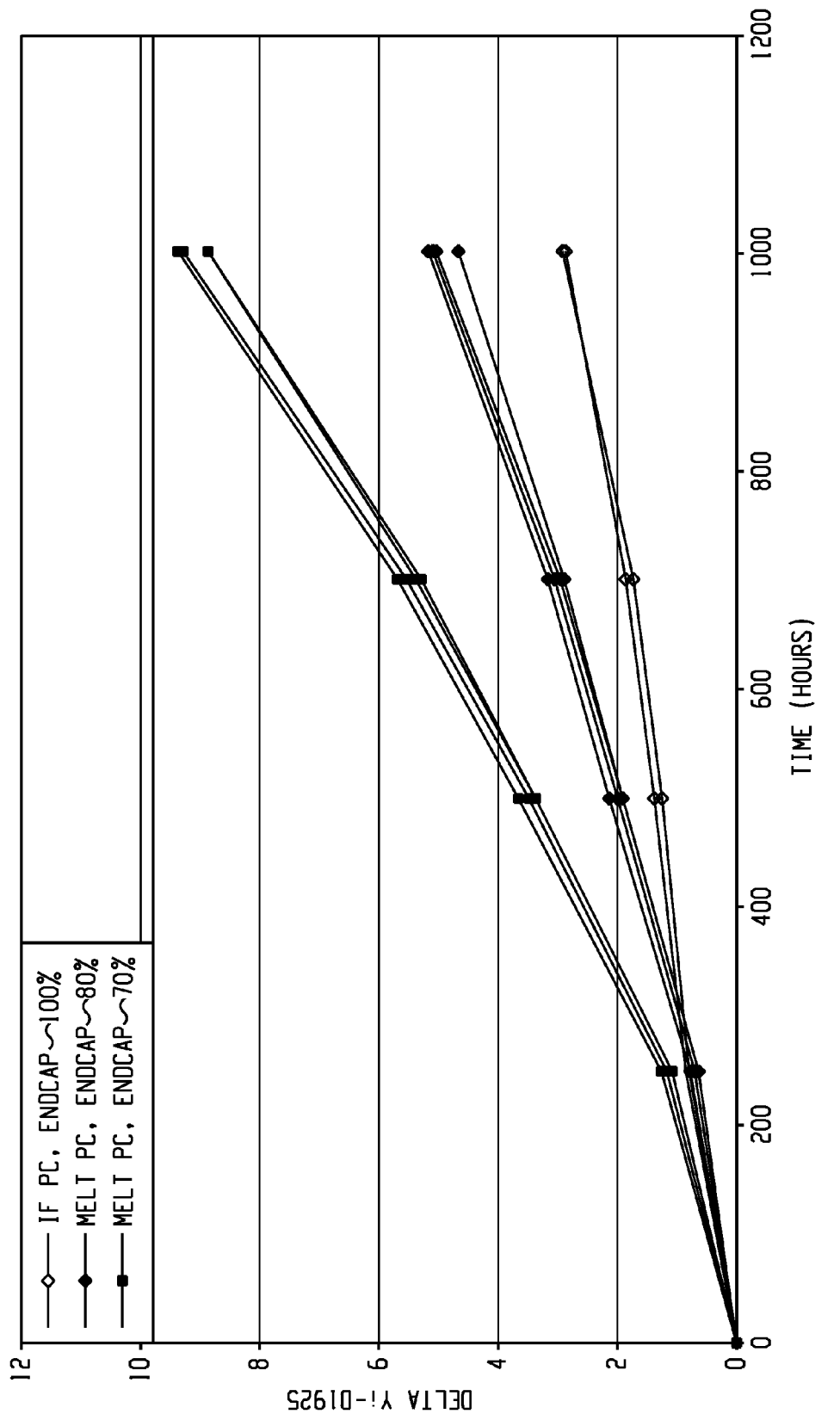
FIG. 6 shows the effect of endcap level in polycarbonate on heat aging performance of the product.

The inventors hereof have found that significant deviations from a targeted molar ratio of aromatic dihydroxy compound to the diaryl carbonate in the synthesis of polycarbonate can have important effects on the conversion and reaction rates as well as on the features and properties of the prepared polycarbonate itself, for example, the molecular weight, the endcap ratio and heat stability, as seen in FIGS. 5a, 5b, and 6.

In attempting to reduce deviations from the targeted molar ratio, the relative amounts of both the aromatic dihydroxy compound the diaryl carbonate are typically controlled using mass flow meters. Even with this type of instrumentation, though, it has been found that significant deviations in the formulated monomer molar ratio exist, which can alter the value of the endcap ratio in the final product and can affect for instance the heat aging stability of the polycarbonate product (FIG. 6).

The inventors have surprisingly found that deviations in the monomer molar ratio can be greatly reduced by using ultrasound meters to control the molar ratio of the diaryl carbonate and the aromatic dihydroxy compound, and accordingly describe herein an improved process to manufacture polycarbonate product having improved properties. For example, the standard deviation from a desired mole ratio can be less than 0.02, less than 0.01, less than 0.005, less than 0.001, or less than 0.0005. A lowest limit of 0.0001 can be achieved, i.e., the standard deviation can be 0.0001 to less than 0.02, or 0.0001 to less than 0.01, or 0.0001 to less than 0.005, or 0.0001 to less than 0.001.

The improved process is based on the utilization of differences in the sound velocity in the diaryl carbonate and in the aromatic dihydroxy compound to determine the relative amounts of the two monomers. Specifically, Applicant found that the sound velocity in the diaryl carbonate is different from the sound velocity in the aromatic dihydroxy compound and this difference is linear with mass composition in a binary mixture of the two at a fixed temperature. Accordingly, by measuring the sound velocity (Vs in meters per second) in a diaryl carbonate/aromatic dihydroxy compound mixture at a fixed temperature, the amounts of the diaryl carbonate and the aromatic dihydroxy compound (in weight percent) in that mixture and the molar ratio (MR) can be derived with simple linear Equation. In addition, Applicants found that a molar control mechanism based on an ultrasound meter offers greater accuracy as compared to a control mechanism based on mass flow meters. Accordingly, polycarbonates manufactured from a process using an ultrasound meter control mechanism can have a consistent endcap ratio thus improved heat aging stability.

A "polycarbonate" as used herein means compositions having repeating structural carbonate units of formula (1)

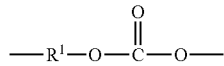

(1)

in which the $R^1$ groups contain aliphatic, alicyclic, and/or or aromatic moieties (e.g., greater than or equal to 30 percent, specifically greater than or equal to 60 percent, of the total number of $R^1$ groups can contain aromatic moieties and the balance thereof are aliphatic, alicyclic, or aromatic). Optionally, each $R^1$ can be a $C_{6-30}$ aromatic group, that is, can contain at least one aromatic moiety. $R^1$ can be derived from a dihydroxy compound of the formula HO—$R^1$—OH, in particular of formula (2)

$$HO\text{-}A^1\text{-}Y^1\text{-}A^2\text{-}OH \quad (2)$$

wherein each of $A^1$ and $A^2$ is a monocyclic divalent aromatic group and $Y^1$ is a single bond or a bridging group having one or more atoms that separate $A^1$ from $A^2$. One atom can separate $A^1$ from $A^2$. Specifically, each $R^1$ can be derived from a bisphenol of formula (3)

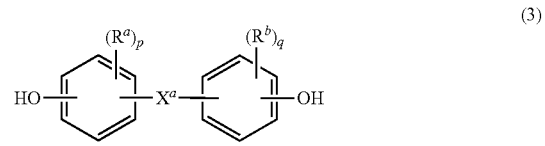

(3)

wherein $R^a$ and $R^b$ are each independently a halogen, $C_{1-12}$ alkoxy, or $C_{1-12}$ alkyl; and p and q are each independently integers of 0 to 4. It will be understood that $R^a$ is hydrogen when p is 0, and likewise $R^b$ is hydrogen when q is 0. Also in formula (3), $X^a$ is a bridging group connecting the two hydroxy-substituted aromatic groups, where the bridging group and the hydroxy substituent of each $C_6$ arylene group are disposed ortho, meta, or para (specifically para) to each other on the $C_6$ arylene group. The bridging group $X^a$ can be single bond, —O—, —S—, —S(O)—, —S(O)$_2$—, —C(O)—, or a $C_{1-18}$ organic group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. p and q can each be 1, and $R^a$ and $R^b$ are each a $C_{1-3}$ alkyl group, specifically methyl, disposed meta to the hydroxy group on each arylene group.

$X^a$ can be a substituted or unsubstituted $C_{3-18}$ cycloalkylidene, a $C_{1-25}$ alkylidene of formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl, or a group of the formula —C(=$R^e$)— wherein $R^e$ is a divalent $C_{1-12}$ hydrocarbon group. Groups of this type include methylene, cyclohexylmethylene, ethylidene, neopentylidene, and isopropylidene, as well as 2-[2.2.1]-bicycloheptylidene, cyclohexylidene, cyclopentylidene, cyclododecylidene, and adamantylidene.

$X^a$ can be a $C_{1-18}$ alkylene group, a $C_{3-18}$ cycloalkylene group, a fused $C_{6-18}$ cycloalkylene group, or a group of the formula —$B^1$-G-$B^2$— wherein $B^1$ and $B^2$ are the same or different $C_{1-6}$ alkylene group and G is a $C_{3-12}$ cycloalkylidene group or a $C_{6-16}$ arylene group. For example, $X^a$ can be a substituted $C_{3-18}$ cycloalkylidene of formula (4)

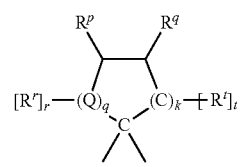

(4)

wherein $R^r$, $R^p$, $R^q$, and $R^t$ are each independently hydrogen, halogen, oxygen, or $C_{1-12}$ hydrocarbon groups; Q is a direct bond, a carbon, or a divalent oxygen, sulfur, or —N(Z)— where Z is hydrogen, halogen, hydroxy, $C_{1-12}$ alkyl, $C_{1-12}$ alkoxy, or $C_{1-12}$ acyl; r is 0 to 2, t is 1 or 2, q is 0 or 1, and k is 0 to 3, with the proviso that at least two of $R^r$, $R^p$, $R^q$, and $R^t$ taken together are a fused cycloaliphatic, aromatic, or heteroaromatic ring. It will be understood that where the fused ring is aromatic, the ring as shown in formula (4) will have an unsaturated carbon-carbon linkage where the ring is fused. When k is one and i is 0, the ring as shown in formula (4) contains 4 carbon atoms, when k is 2, the ring as shown in formula (4) contains 5 carbon atoms, and when k is 3, the ring contains 6 carbon atoms. Two adjacent groups (e.g., $R^q$ and $R^t$ taken together) can form an aromatic group or $R^q$ and $R^t$ taken together can form one aromatic group and $R^r$ and $R^p$ taken together form a second aromatic group. When $R^q$ and $R^t$ taken together form an aromatic group, $R^p$ can be a double-bonded oxygen atom, i.e., a ketone.

Bisphenols wherein $X^a$ is cycloalkylidene of formula (4) can be used in the manufacture of polycarbonates containing phthalimidine carbonate units of formula (1a)

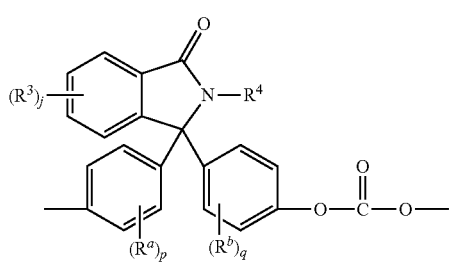
(1a)

wherein $R^a$, $R^b$, p, and q are as in formula (4), $R^3$ is each independently a $C_{1-6}$ alkyl group, j is 0 to 4, and $R_4$ is a $C_{1-6}$ alkyl, phenyl, or phenyl substituted with up to five $C_{1-6}$ alkyl groups. The phthalimidine carbonate units can be of formula (1b)

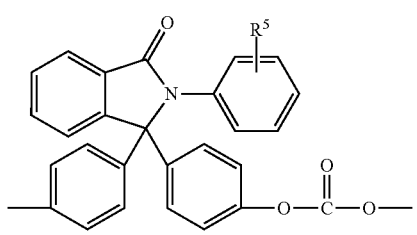
(1b)

wherein $R^5$ is hydrogen or a $C_{1-6}$ alkyl. $R^5$ can be hydrogen. Carbonate units (1b) wherein $R^5$ is hydrogen can be derived from 2-phenyl-3,3'-bis(4-hydroxy phenyl)phthalimidine (also known as N-phenyl phenolphthalein bisphenol, or "PPPBP") (also known as 3,3-bis(4-hydroxyphenyl)-2-phenylisoindolin-1-one).

Other bisphenol carbonate repeating units of this type are the isatin carbonate units of formula (1c) and (1d)

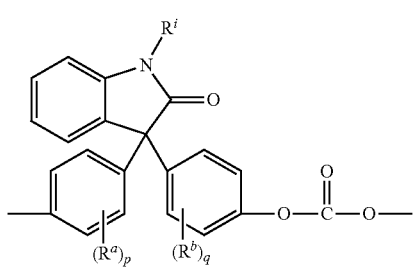
(1c)

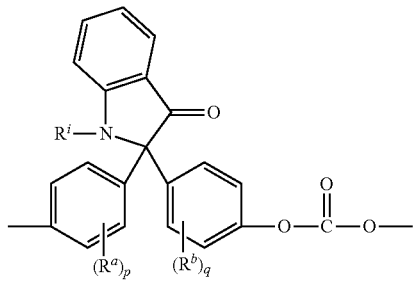
(1d)

wherein $R^a$ and $R^b$ are each independently $C_{1-12}$ alkyl, p and q are each independently 0 to 4, and $R^i$ is $C_{1-12}$ alkyl, phenyl, optionally substituted with 1 5 to $C_{1-10}$ alkyl, or benzyl optionally substituted with 1 to 5 $C_{1-10}$ alkyl. $R^a$ and $R^b$ can each be methyl, p and q can each independently be 0 or 1, and $R^i$ can be $C_{1-4}$ alkyl or phenyl.

Other examples of bisphenol carbonate units derived from bisphenols (3) wherein $X^a$ is a substituted or unsubstituted $C_{3-18}$ cycloalkylidene (4) include the cyclohexylidene-bridged, alkyl-substituted bisphenol of formula (1e)

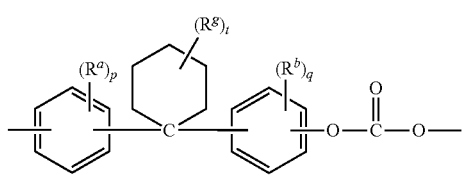
(1e)

wherein $R^a$ and $R^b$ are each independently $C_{1-12}$ alkyl, $R^g$ is $C_{1-12}$ alkyl, p and q are each independently 0 to 4, and t is 0 to 10. At least one of each of $R^a$ and $R^b$ can be disposed meta to the cyclohexylidene bridging group. $R^a$ and $R^b$ can each independently be $C_{1-4}$ alkyl, $R^g$ can be $C_{1-4}$ alkyl, p and q can each be 0 or 1, and t is 0 to 5. $R^a$, $R^b$, and $R^g$ can be each methyl, r and s can be each 0 or 1, and t can be 0 or 3, specifically 0.

Examples of other bisphenol carbonate units derived from bisphenols (3) wherein $X^a$ is a substituted or unsubstituted $C_{3-18}$ cycloalkylidene (1) include adamantyl units (1f) and units (1g)

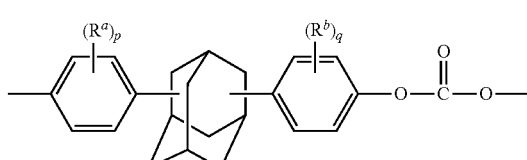
(1f)

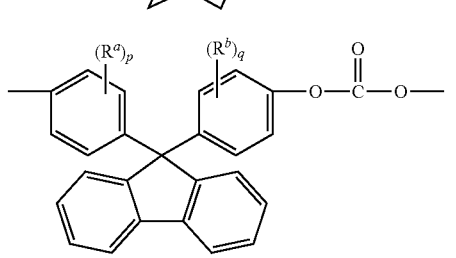
(1g)

wherein $R^a$ and $R^b$ are each independently $C_{1-12}$ alkyl, and p and q are each independently 1 to 4. At least one of each of $R^a$ and $R^b$ can be disposed meta to the cycloalkylidene bridging group. $R^a$ and $R^b$ can each independently be $C_{1-3}$ alkyl, and p and q can be each 0 or 1. $R^a$, $R^b$ can be each methyl, p and q can each be 0 or 1. Carbonates containing units (1a) to (1g) are useful for making polycarbonates with high glass transition temperatures (Tg) and high heat distortion temperatures.

Other possible aromatic dihydroxy compounds of the formula HO—$R^1$—OH include compounds of formula (6)

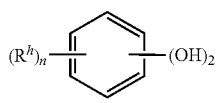

(6)

wherein each $R^h$ is independently a halogen atom, a $C_{1-10}$ hydrocarbyl such as a $C_{1-10}$ alkyl group, a halogen-substituted $C_{1-10}$ alkyl group, a $C_{6-10}$ aryl group, or a halogen-substituted $C_{6-10}$ aryl group, and n is 0 to 4. The halogen is usually bromine.

Some illustrative examples of specific aromatic dihydroxy compounds (herein also referred to as dihydroxy reactants) include the following: 4,4'-dihydroxybiphenyl, 1,6-dihydroxynaphthalene, 2,6-dihydroxynaphthalene, bis(4-hydroxyphenyl)methane, bis(4-hydroxyphenyl)diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl)phenylmethane, 2,2-bis(4-hydroxy-3-bromophenyl)propane, 1,1-bis(hydroxyphenyl)cyclopentane, 1,1-bis(4-hydroxyphenyl)cyclohexane, 1,1-bis(4-hydroxyphenyl)isobutene, 1,1-bis(4-hydroxyphenyl)cyclododecane, trans-2,3-bis(4-hydroxyphenyl)-2-butene, 2,2-bis(4-hydroxyphenyl)adamantane, alpha,alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl)sulfone, 9,9-bis(4-hydroxyphenyl)fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalimide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluoro hydroquinone, 2,3,5,6-tetrabromo hydroquinone, or the like, or combinations comprising at least one of the foregoing dihydroxy compounds.

Specific examples of bisphenol compounds of formula (3) include 1,1-bis(4-hydroxyphenyl)methane, 1,1-bis(4-hydroxyphenyl)ethane, 2,2-bis(4-hydroxyphenyl)propane (hereinafter "bisphenol A" or "BPA"), 2,2-bis(4-hydroxyphenyl)butane, 2,2-bis(4-hydroxyphenyl)octane, 1,1-bis(4-hydroxyphenyl)propane, 1,1-bis(4-hydroxyphenyl)n-butane, 2,2-bis(4-hydroxy-2-methylphenyl)propane, 1,1-bis(4-hydroxy-t-butylphenyl)propane, 3,3-bis(4-hydroxyphenyl)phthalimidine, 2-phenyl-3,3-bis(4-hydroxyphenyl)phthalimidine (PPPBP), and 1,1-bis(4-hydroxy-3-methylphenyl)cyclohexane (DMBPC). Combinations comprising at least one of the foregoing dihydroxy compounds can also be used. The polycarbonate can be a linear homopolymer derived from bisphenol A, in which each of $A^1$ and $A^2$ can be p-phenylene, and $Y^1$ can be isopropylidene in formula (3).

"Polycarbonates" as used herein also includes homopolycarbonates (wherein each $R^1$ in the polymer is the same), copolymers comprising different $R^1$ moieties in the carbonate ("copolycarbonates"), copolymers comprising carbonate units and other types of polymer units, such as ester units, and combinations comprising at least one of homopolycarbonates and/or copolycarbonates.

A specific type of copolymer is a polyester carbonate, also known as a polyester-polycarbonate. Such copolymers further contain, in addition to recurring carbonate chain units of formula (1), repeating units of formula (7)

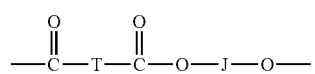

(7)

wherein J is a divalent group derived from a dihydroxy compound, and can be, for example, a $C_{2-10}$ alkylene, a $C_{6-20}$ cycloalkylene a $C_{6-20}$ arylene, or a polyoxyalkylene group in which the alkylene groups contain 2 to 6 carbon atoms, specifically 2, 3, or 4 carbon atoms; and T is a divalent group derived from a dicarboxylic acid, and can be, for example, a $C_{2-10}$ alkylene, a $C_{6-20}$ cycloalkylene, or a $C_{6-20}$ arylene. Copolyesters containing a combination of different T and/or J groups can be used. The polyesters can be branched or linear.

J can be a $C_{2-30}$ alkylene group having a straight chain, branched chain, or cyclic (including polycyclic) structure. J can be derived from an aromatic dihydroxy compound of formula (3) above. J can be derived from an aromatic dihydroxy compound of formula (4) above. J can be derived from an aromatic dihydroxy compound of formula (6) above.

Aromatic dicarboxylic acids that can be used to prepare the polyester units include isophthalic or terephthalic acid, 1,2-di(p-carboxyphenyl)ethane, 4,4'-dicarboxydiphenyl ether, 4,4'-bisbenzoic acid, or a combination comprising at least one of the foregoing acids. Acids containing fused rings can also be present, such as in 1,4-, 1,5-, or 2,6-naphthalenedicarboxylic acids. Specific dicarboxylic acids include terephthalic acid, isophthalic acid, naphthalene dicarboxylic acid, cyclohexane dicarboxylic acid, or a combination comprising at least one of the foregoing acids. A specific dicarboxylic acid comprises a combination of isophthalic acid and terephthalic acid wherein the weight ratio of isophthalic acid to terephthalic acid is 91:9 to 2:98. J can be a $C_{2-6}$ alkylene group and T can be p-phenylene, m-phenylene, naphthalene, a divalent cycloaliphatic group, or a combination thereof. This class of polyester includes the poly(alkylene terephthalates).

The molar ratio of ester units to carbonate units in the copolymers can vary broadly, for example 1:99 to 99:1, specifically 10:90 to 90:10, more specifically 25:75 to 75:25, depending on the desired properties of the final composition.

The polyester unit of a polyester-polycarbonate can be derived from the reaction of a combination of isophthalic and terephthalic diacids (or derivatives thereof) with resorcinol. The polyester unit of a polyester-polycarbonate can be derived from the reaction of a combination of isophthalic acid and terephthalic acid with bisphenol A. The polycarbonate units can be derived from bisphenol A. The polycarbonate units can be derived from resorcinol and bisphenol A in a molar ratio of resorcinol carbonate units to bisphenol A carbonate units of 1:99 to 99:1.

The polycarbonate can be made by a melt polymerization process, which can be a continuous melt process. Generally, in a melt polymerization process, polycarbonates can be prepared by co-reacting, in a molten state, a dihydroxy reactant and a diaryl carbonate (herein also referred to as a diaryl carbonate ester), such as diphenyl carbonate.

The diaryl carbonate can have the formula (I)

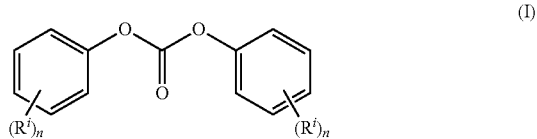

(I)

wherein n is an integer 1 to 3 and each $R_2$ is independently a linear or branched, optionally substituted $C_{1-34}$ alkyl (specifically $C_{1-6}$ alkyl, more specifically $C_{1-4}$ alkyl), $C_{1-34}$ alkoxy (specifically $C_{1-6}$ alkoxy, more specifically $C_{1-4}$ alkoxy), $C_{5-34}$ cycloalkyl, $C_{7-34}$ alkylaryl $C_{6-34}$ aryl, a halogen radical (specifically a chlorine radical), or —C(=O)OR' wherein R' is H, linear or branched $C_{1-34}$ alkyl (specifically $C_{1-6}$ alkyl, more specifically $C_{1-4}$ alkyl), $C_{1-34}$ alkoxy (specifically $C_{1-16}$ alkoxy, specifically $C_{1-4}$ alkoxy), $C_{5-34}$ cycloalkyl, $C_{7-34}$ alkylaryl, or $C_{6-34}$ aryl.

The diaryl carbonate (I) can be diphenyl carbonate, methylphenyl-phenyl carbonates and di-(methylphenyl)carbonates (wherein the methyl group can be in any desired position on the phenyl rings), dimethylphenyl-phenyl carbonates and di-(dimethylphenyl)carbonates (wherein the methyl groups can be in any desired position on the phenyl rings), chlorophenyl-phenyl carbonates and di-(chlorophenyl)carbonates (wherein the methyl group can be in any desired position on the phenyl rings), 4-ethylphenyl-phenyl carbonate, di-(4-ethylphenyl)carbonate, 4-n-propylphenyl-phenyl carbonate, di-(4-n-propylphenyl)carbonate, 4-isopropylphenyl-phenyl carbonate, di-(4-isopropylphenyl)carbonate, 4-n-butylphenyl-phenyl carbonate, di-(4-n-butylphenyl)carbonate, 4-isobutylphenyl-phenyl carbonate, di-(4-isobutylphenyl) carbonate, 4-tert-butylphenyl-phenyl carbonate, di-(4-tert-butylphenyl)carbonate, 4-n-pentylphenyl-phenyl carbonate, di-(4-n-pentylphenyl)carbonate, 4-n-hexylphenyl-phenyl carbonate, di-(4-n-hexylphenyl)carbonate, 4-isooctylphenyl-phenyl carbonate, di-(4-isooctylphenyl)carbonate, 4-n-nonylphenyl-phenyl carbonate, di-(4-n-nonyl-phenyl)carbonate, 4-cyclohexylphenyl-phenyl carbonate, di-(4-cyclohexylphenyl)carbonate, 4-(1-methyl-1-phenylethyl)-phenyl-phenyl carbonate, di-[4-(1-methyl-1-phenylethyl)-phenyl]carbonate, biphenyl-4-yl-phenyl carbonate, di-(biphenyl-4-yl)carbonate, (1-naphthyl)-phenyl carbonate, (2-naphthyl)-phenyl carbonate, di-(1-naphthyl)carbonate, di-(2-naphthyl)carbonate, 4-(1-naphthyl)-phenyl-phenyl carbonate, 4-(2-naphthyl)-phenyl-phenyl carbonate, di-[4-(1-naphthyl)-phenyl] carbonate, di-[4-(2-naphthyl)phenyl]carbonate, 4-phenoxyphenyl-phenyl carbonate, di-(4-phenoxyphenyl) carbonate, 3-pentadecylphenyl-phenyl carbonate, di-(3-pentadecylphenyl)carbonate, 4-tritylphenyl-phenyl carbonate, di-(4-tritylphenyl)carbonate, methyl salicylate-phenyl carbonate, di-(methyl salicylate) carbonate, ethyl salicylate-phenyl carbonate, di-(ethyl salicylate) carbonate, n-propyl salicylate-phenyl carbonate, di-(n-propyl salicylate) carbonate, isopropyl salicylate-phenyl carbonate, di-(isopropyl salicylate) carbonate, n-butyl salicylate-phenyl carbonate, di-(n-butyl salicylate)carbonate, isobutyl salicylate-phenyl carbonate, di-(isobutyl salicylate) carbonate, tert-butyl salicylate-phenyl carbonate, di-(tert-butyl salicylate) carbonate, di-(phenyl salicylate)-carbonate, di-(benzyl salicylate) carbonate, and combinations comprising one or more of the foregoing. The diaryl carbonate can comprise diphenyl carbonate.

The diaryl carbonate can have electron-withdrawing substituents on the aryls. Examples of specifically useful diaryl carbonates with electron withdrawing substituents include bis(4-nitrophenyl)carbonate, bis(2-chlorophenyl)carbonate, bis(4-chlorophenyl)carbonate, bis(methyl salicyl)carbonate, bis(4-methylcarboxylphenyl)carbonate, bis(2-acetylphenyl) carboxylate, bis(4-acetylphenyl)carboxylate, or a combination comprising at least one of the foregoing esters. The diaryl carbonate to dihydroxy reactant can be introduced to, for example, a mixer or a reactor in a molar ratio of 2:1 to 1:2, specifically in a molar ratio of 1.5:1 to 1:1.5, more specifically in a molar ratio of 1.05:1 to 1:1.05, even more specifically in a molar ratio of 1:1.

In addition, transesterification catalyst(s) can be employed in the polymerization of the aromatic dihydroxy compound and the diaryl carbonate. Catalysts used in the melt transesterification polymerization production of polycarbonates can include alpha and/or beta catalysts. Beta catalysts are typically volatile and degrade at elevated temperatures. Beta catalysts are therefore preferred for use at early low-temperature polymerization stages. Alpha catalysts are typically more thermally stable and less volatile than beta catalysts.

The alpha catalyst can comprise a source of alkali or alkaline earth ions. The sources of these ions include alkaline earth hydroxides such as magnesium hydroxide and calcium hydroxide. Sources of alkali metal ions can include the alkali metal hydroxides such as illustrated by lithium hydroxide, sodium hydroxide, potassium hydroxide and combinations comprising at least one of the foregoing. Examples of alkaline earth metal hydroxides are calcium hydroxide, magnesium hydroxide, and combinations comprising at least one of the foregoing. Of these, sodium hydroxide is particularly desirable. The alpha catalyst typically will be used in an amount sufficient to provide $1\times10^{-2}$ to $1\times10^{-8}$ moles, specifically, $1\times10^{-4}$ to $1\times10^{-7}$ moles of metal hydroxide per mole of the dihydroxy compounds employed. Other possible sources of alkaline earth and alkali metal ions include salts of carboxylic acids (such as sodium acetate) and derivatives of ethylene diamine tetraacetic acid (EDTA) (such as EDTA tetrasodium salt, and EDTA magnesium disodium salt), as well as combinations comprising at least one of the foregoing. For example, the alpha catalyst can comprise alkali metal salt(s) of a carboxylic acid, alkaline earth metal salt(s) of a carboxylic acid, or a combination comprising at least one of the foregoing. In another example, the alpha catalyst comprises $Na_2Mg$ EDTA or a salt thereof.

The alpha transesterification catalyst can also, or alternatively, comprise salt(s) of a non-volatile inorganic acid. For example, the alpha catalyst can comprise salt(s) of a non-volatile inorganic acid such as $NaH_2PO_3$, $NaH_2PO_4$, $Na_2HPO_3$, $KH_2PO_4$, $CsH_2PO_4$, $Cs_2HPO_4$, mixed salts of phosphoric acid, such as $NaKHPO_4$, $CsNaHPO_4$, $CsKHPO_4$, and the like, and combinations comprising at least one of the foregoing. Alternatively, or in addition, the alpha transesterification catalyst can comprise mixed alkali metal salt(s) of phosphoric acid, such as $NaKHPO_4$, $CsNaHPO_4$, $CsKHPO_4$, and combinations comprising at least one of the foregoing. The alpha transesterification catalyst can also comprise mixed alkali metal salt(s) of carboxylic acid, such as $Cs_2CO_3$, $NaHCO_3$, $Na_2CO_3$, and combinations comprising at least one of the foregoing.

Possible beta catalyst(s) can comprise a quaternary ammonium compound, a quaternary phosphonium compound, or a combination comprising at least one of the foregoing. The quaternary ammonium compound can be a compound of the structure $(R^4)_4N^+X^-$, wherein each $R^4$ is the same or different, and is a $C_{1-20}$ alkyl, a $C_{4-20}$ cycloalkyl, or a $C_{4-20}$ aryl; and $X^-$ is an organic or inorganic anion, for example a hydroxide, halide, acetate, phenoxide, carboxylate, sulfonate, sulfate, formate, carbonate, or bicarbonate. Examples of organic quaternary ammonium compounds include tetramethyl ammonium hydroxide, tetrabutyl ammonium hydroxide, tetramethyl ammonium acetate, tetramethyl ammonium formate, tetrabutyl ammonium acetate, and combinations comprising at least one of the foregoing. Tetramethyl ammonium hydroxide is often used.

The quaternary phosphonium compound can be a compound of the structure $(R^5)_4P^+X^-$, wherein each $R^5$ is the same or different, and is a $C_{1-20}$ alkyl, a $C_{4-20}$ cycloalkyl, or a $C_{4-20}$ aryl; and $X^-$ is an organic or inorganic anion, for example a hydroxide, halide, carboxylate, sulfonate, sulfate, formate, carbonate, or bicarbonate. Where $X^-$ is a polyvalent anion such as carbonate or sulfate it is understood that the positive and negative charges in the quaternary ammonium and phosphonium structures are properly balanced. For example, where $R^{20}$ to $R^{23}$ are each methyls and $X^-$ is carbonate, it is understood that $X^-$ represents 2 $(CO_3^{-2})$. Examples of organic quaternary phosphonium compounds include tetramethyl phosphonium hydroxide, tetramethyl phosphonium acetate, tetramethyl phosphonium formate, tetrabutyl phosphonium hydroxide, tetrabutyl phosphonium acetate (TBPA), tetraphenyl phosphonium acetate, tetraphenyl phosphonium phenoxide, and combinations comprising at least one of the foregoing. TBPA is often used.

The amount of beta catalyst employed is typically based upon the total number of moles of dihydroxy compound employed in the polymerization reaction. When referring to the ratio of beta catalyst, for example, phosphonium salt, to all dihydroxy compounds employed in the polymerization reaction, it is convenient to refer to moles of phosphonium salt per mole of the dihydroxy compound(s), meaning the number of moles of phosphonium salt divided by the sum of the moles of each individual dihydroxy compound present in the reaction mixture. The amount of beta catalyst (e.g., organic ammonium or phosphonium salts) employed typically will be $1 \times 10^{-2}$ to $1 \times 10^{-5}$, specifically $1 \times 10^{-3}$ to $1 \times 10^{-4}$ moles per total mole of the dihydroxy compounds in the reaction mixture.

There are several methods by which diaryl carbonate can be produced. One method for producing diaryl carbonate includes the decarbonylation of a diaryl oxalate (such as diphenyl oxalate) in the presence of a decarbonylation catalyst while removing a carbon monoxide by product. The decarbonylation reaction can occur in the liquid phase. The diaryl oxalate can comprise a diaryl oxalate of the formula: $ArO(C=O)-(C=O)OAr$, where each Ar independently can be an aromatic hydrocarbon group having 6 to 14 carbon atoms, for example, Ar can be a phenyl group, which can be substituted with at least one selected from alkyl groups having 1 to 6 carbon atoms (such as methyl, ethyl, propyl, butyl, pentyl, and hexyl), alkoxy groups having 1 to 6 carbon atoms (such as methoxy, propoxy, butoxy, pentoxy, and hexoxy), and halogen atoms (such as fluorine, chlorine, bromine, and iodine). The diaryl oxalate can comprise diphenyl oxalate, m-cresyl oxalate, m-cresyl phenyl oxalate, p-cresyl oxalate, p-cresyl phenyl oxalate, dinaphthyl oxalate, bis(diphenyl) oxalate, bis(chlorophenyl)oxalate, or a combination comprising of one or more of the forgoing. The diaryl oxalate can contain less than or equal to 5 parts per million by weight (ppm), specifically, less than or equal to 2 ppm of a hydrolysable halogen.

The diaryl oxalate can be prepared by transesterifying a dialkyl oxalate (such as dimethyl oxalate) with a hydroxyaryl compound (such as phenol) in the presence of a transesterification catalyst, where the transesterification reaction can occur in the liquid phase. The dialkyl oxalate can comprise one or more lower dialkyl oxalates of which the alkyl group comprises 1 to 6 carbon atoms, for example dimethyl oxalate, diethyl oxalate, dipropyl oxalate, dibutyl oxalate, dipentyl oxalate, and dihexyl oxalate.

The transesterification catalyst useful for the preparation of the diaryl oxalate from the dialkyl oxalate and the hydroxyaryl compound can comprise at least one of, for example, compounds and complexes of alkali metals, compounds and complexes of cadmium and zirconium, lead-containing compounds, iron-containing compounds, copper group metal compounds, silver-containing compounds, zinc-containing compounds, organic tin compounds, and Lewis acid compounds of aluminum, titanium, and vanadium. The decarbonylation catalyst can comprise at least one organic phosphorus compound (such as an organic phosphine compound, an organic phosphine oxide compound, an organic phosphine dihalide compound, and an organic phosphonium salt compound). The decarbonylation catalyst can contain a halogen, for example, on the phosphorus containing compound or as a separate halogen compound.

Another method for producing diaryl carbonate includes reacting an aromatic hydroxy compound and carbon monoxide in the presence of oxygen, where the reaction can be facilitated by a catalyst and an optional organic salt. For example, the reaction can be the oxidative carbonylation of phenol, where the reaction can occur in a fixed-bed reactor or in an agitated tank reactor. Suitable catalysts for the oxidative carbonylation of aromatic hydroxy compounds include a palladium catalyst. The palladium catalyst can be in solvated form (such as $PdBr_2$ promoted with transition metal oxides and solvated promoters, including one or more of $N(Bu)_4Br$, $Mn(AcAc)_2$, $NaO(C_6H_5)$ and the like), suspended form with Pd supported on pulverized $TiO_2$, or extrudated form with Pd supported on rare earth metal oxide. The palladium catalyst can comprise $Pd(OAc)_2$/hydrotalcite. As used herein Bu means butyl, AcAc means acetylacetonate, and OAc means acetate. The catalyst can comprise a cocatalyst, such as a cesium compound, a manganese compound, a cobalt compound, a copper compound, hydroquinone, benzoquinone, naphthoquinone, or a combination comprising one or more of the foregoing. The organic salt can comprise, for example, $"Bu_4NBr$, $"Bu_4PBr$, PPNBr, and the like.

Other methods for producing diaryl carbonate include reacting an aromatic hydroxy compound with phosgene in either the gas or liquid phase, for example, the direct phosgenation of phenol and reacting an aromatic hydroxy compound with a dialkyl carbonate, where said reactions can occur in the presence of a transesterification catalyst. The aromatic hydroxy compound and either phosgene or the dialkyl carbonate can be added in a molar ratio of 1:0.1 to 1:10, specifically 1:0.2 to 1:5, more specifically 1:0.5 to 1:3. The indicated molar ratio does not take into account any recycled components that can be added back to the production column.

A catalyst can be used to facilitate the reaction between the aromatic hydroxy compound and either phosgene or the dialkyl carbonate. The catalyst can be a homogeneous catalyst and/or a heterogeneous catalyst, wherein a heterogeneous catalyst comprises two or more catalysts. The catalyst can comprise hydrides, oxides, hydroxides, alcoholates, amides and other salts of alkali and alkaline earth metals, such as of lithium, sodium, potassium, rubidium, cesium, magnesium and calcium, specifically lithium, sodium, potassium, magnesium, calcium, or a combination comprising one or more of the foregoing. Salts of the alkali and alkaline earth metals can also be salts of organic or inorganic acids, such as of acetic acid, propionic acid, butyric acid, benzoic acid, stearic acid, carbonic acid (carbonates or hydrogen carbonates), phosphoric acid, hydrocyanic acid, thiocyanic acid, boric acid, cinnamic acid, $C_{14}$-stannonic acids, antimonic acid, or a combination comprising one or more of the foregoing. Suitable compounds of the alkali and alkaline earth metals can be the oxides, hydroxides, alcoholates, acetates, propionates, benzoates, carbonates, and hydrogen carbonates. The mentioned alkali or alkaline earth metal compounds can be used in amounts of 0.001 to 2 weight percent (wt %), specifically 0.005 to 0.9 wt %, and more specifically 0.01 to 0.5 wt %, based on the weight of the reaction mixture to be reacted.

Further catalysts that can be used can comprise a metal such as titanium, lead, tin, zirconium, molybdenum, niobium, vanadium, uranium, iron, zinc, aluminum, yttrium, lanthanum, hafnium, tungsten, neodymium, samarium, ytterbium, copper, or a combination comprising one or more of the foregoing. Such metals can be used in metal catalyst compounds such as $AlX_3$, $TiX_3$, $UX_4$, $TiX_4$, $VOX_3$, $VX_5$, $ZnX_2$, $FeX_3$, $PbX_2$ and $SnX_4$, wherein X represents halogen, acetoxy, alkoxy, aryloxy radicals, or a combination comprising one or more of the foregoing. The metal compound of $AlX_3$, $TiX_4$, $PbX_2$, and $SnX_4$ can comprise titanium tetrachloride, titanium tetramethoxide, titanium tetraphenoxide, titanium tetraethoxide, titanium tetraisopropylate, titanium tetradodecylate, tin tetraisooctylate and aluminium triisopropylate. The mentioned metal compounds can be used in an amount of 0.001 to 15 wt %, more specifically 0.005 to 5 wt %, and even more specifically 0.01 to 5 wt %, based on the weight of the reaction mixture to be reacted.

Further catalysts which can be used can be organotin compounds of the general formula $(R^{11})_{4-x}$—$Sn(Y)_x$, wherein Y represents a radical $OCOR^{12}$, OH, or $OR^{12}$, wherein $R^{12}$ represents $C_{1-12}$ alkyl, $C_{6-12}$ aryl or $C_{7-13}$ alkylaryl, $R^{11}$ independently of $R^{12}$ has the meaning of $R^{12}$ and x represents an integer 1 to 3; dialkyltin compounds having from 1 to 12 carbon atoms in the alkyl radical; or bis-(trialkyltin) compounds, for example trimethyltin acetate, triethyltin benzoate, tributyltin acetate, triphenyltin acetate, dibutyltin diacetate, dibutyltin dilaurate, dioctyltin dilaurate, dibutyltin adipinate, dibutyldimethoxytin, dimethyltin glycolate, dibutyldiethoxytin, triethyltin hydroxide, hexaethylstannoxane, hexabutylstannoxane, dibutyltin oxide, dioctyltin oxide, butyltin triisooctylate, octyltin triisooctylate, butylstannonic acid, octylstannonic acid, or a combination comprising one or more of the foregoing. The organotin compound can be used in an amount of 0.001 to 20 wt %. The organotin compound can comprise polymeric tin compounds of the formula —[—$RR^{11}Sn$—O—]—, in which R and $R^{11}$ independently of one another have the meaning given above for $R^{12}$, for example poly[oxy(dibutylstannylene)], poly[oxy(dioctyl stannylene)], poly[oxy(butylphenyl stannylene)], and poly [oxy(diphenylstannylene)], polymeric hydroxystannoxanes of the formula —[—$RSn(OH)$—O—]—, for example, poly (ethylhydroxystannoxane), poly(butylhydroxystannoxane), poly(octylhydroxysnoxane), poly(undecylhydroxystannoxane), and poly(dodecylhydroxystannoxanes), or a combination comprising one or more of the foregoing. The polymeric tin compounds can be used in an amount of 0.001 to 20 wt %, specifically 0.005 to 5 wt %, based on dialkyl carbonate. Further tin compounds, which can be used are Sn(II) oxides of the general formula X—$R^{13}Sn$—O—$R^{13}Sn$—Y, wherein X and Y independently of one another represent OH, SCN, $OR^{14}$, $OCOR^{14}$ or halogen and $R^{13}$ is $C_{1-12}$ alkyl, $C_{6-12}$ aryl or $C_{7-13}$ alkylaryl, wherein $R^{14}$ has the meaning given above for $R^{12}$.

Further catalysts are lead compounds, optionally together with triorganophosphanes, a chelate compound or an alkali metal halide, for example lead diphenoxide, $Pb(OH)_2$·$2PbCO_3$, $Pb(OCO—CH_3)_2$, $Pb(OCO—CH_3)_2$·$2LiCl$, $Pb(OCO—CH_3)_3$·$2PPh_3$, as well as other lead(II) and lead (IV) compounds, such as PbO, $PbO_2$, red lead, plumbites and plumbates, or a combination comprising one or more of the foregoing. The lead compounds can be present in an amount of 0.001 to 1, specifically, 0.005 to 0.25 mole per mole of dialkyl carbonate.

Further catalysts are iron (III) acetate, also copper salts and/or metal complexes, for example of alkali, zinc, titanium, iron, and combinations comprising one or more of the foregoing. Said catalysts can be present in an amount of 0.001 to 1, specifically, 0.005 to 0.25 mole per mole of dialkyl carbonate.

It is further possible to use heterogeneous catalyst systems. Such systems are, for example, mixed oxides of silicon and titanium, which are obtainable by common hydrolysis of silicon and titanium halides or titanium dioxides having a high Brunaer, Emmet and Taller (BET) surface area of greater than or equal to 20 meters squared per gram ($m^2/g$).

The catalyst, when homogeneous, can be introduced to the reaction mixture in dissolved or suspended form together with the stream containing the aromatic hydroxy compound. Alternatively, the catalyst can be introduced, for example in the reaction alcohol or a suitable inert solvent. A heterogeneous catalyst can be used in a packed bed, a column, or in special catalytic distillation arrangements, as well as in other arrangements.

The diaryl carbonate can be a purified diaryl carbonate such that greater than or equal to 80% of one or more metal contaminant(s), specifically, greater than or equal to 90% has been removed. Specifically, the purified diaryl carbonate can comprise one or more of less than or equal to 33 parts per billion by weight (ppb), specifically less than or equal to 20 ppb of molybdenum; less than or equal to 33 ppb, specifically less than or equal to 20 ppb vanadium; less than or equal to 33 ppb, specifically less than or equal to 20 ppb chromium; less than or equal to 33 ppb, specifically less than or equal to 20 ppb titanium; less than or equal to 163 ppb, specifically less than or equal to 100 ppb of nickel; less than or equal to 163 ppb, specifically less than or equal to 100 ppb zirconium; and less than the detection limit of iron.

Figure 1:
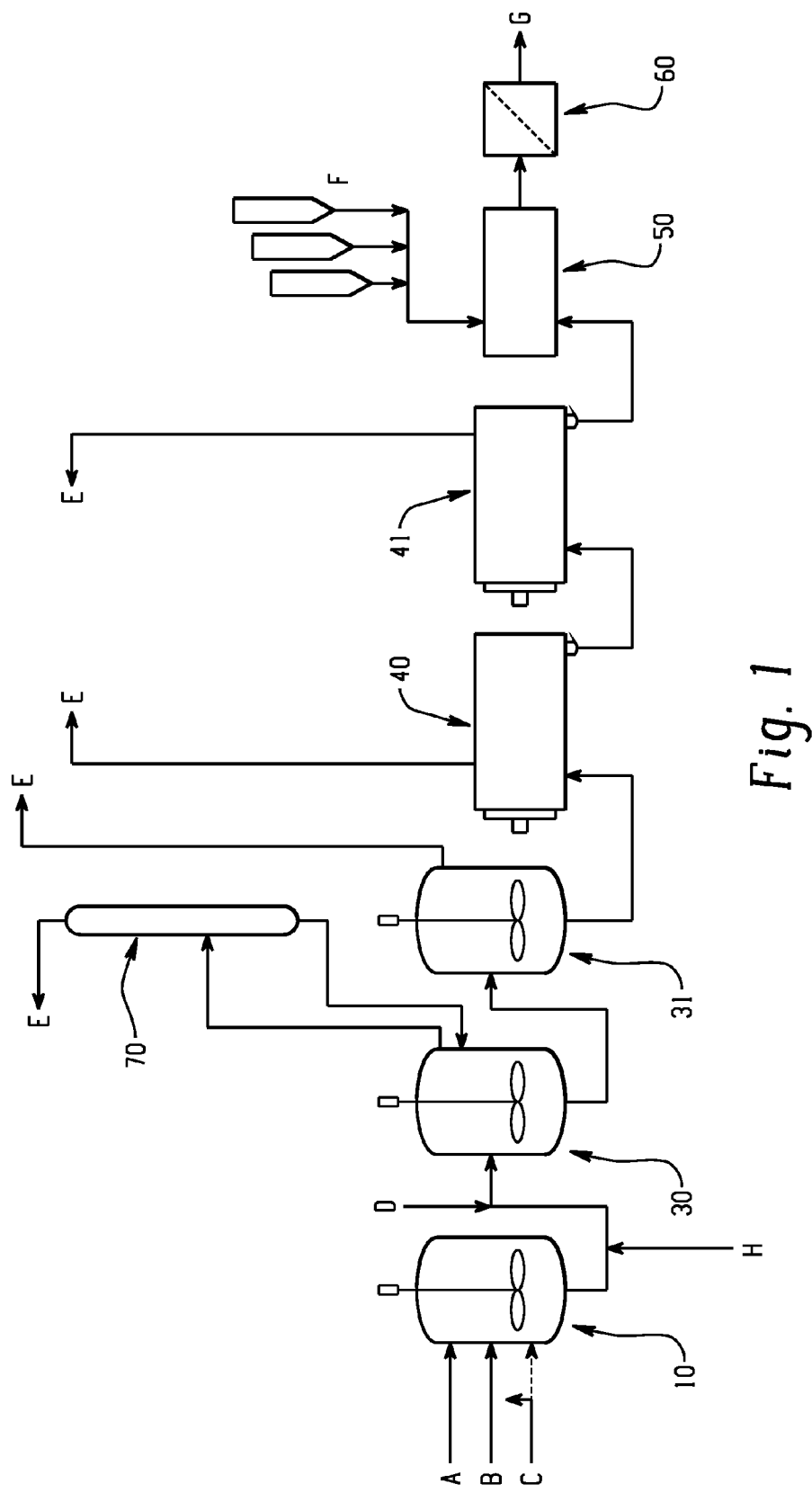
FIG. 1 is a schematic representation of a continuous melt polymerization process to prepare polycarbonate.

An exemplary polymerization process is illustrated in FIG. 1. The polymerization units can comprise monomer pre-mixer(s) (10), two or more pre-polymerization vessels (30, 31), polymerizer(s) (40, 41), an extruder(s) (50), a filter(s) (60), a scrubber(s) (70), or combinations comprising one or more of the foregoing. In FIG. 1, the dihydroxy reactant (A), the diaryl carbonate (B), and the catalyst (C) are added to a pre-mixer (10). Additional diaryl carbonate (D) and catalyst (H) can optionally be added and the reactants are sent to pre-polymerization vessels (30, 31). Phenol by-product (E) is removed from the pre-polymerization vessels (30, 31) and from the polymerizers (40, 41). Any additive (F) is added to the polymerized polycarbonate in the extruder (50). The extruded polycarbonate is filtered in a melt filter (60) to produce polycarbonate pellets (G). As used herein, "molar ratio" in this process refers to overall molar ratio, which is the sum of the moles of diaryl carbonate flowstreams B plus D divided by the moles of dihydroxy stream A.

For example, the starting raw materials can comprise diphenyl carbonate (DPC) and Bisphenol A (BPA) in a fixed molar ratio, for example adjusted to a 1:1 ratio and can be fed together with a catalyst into a pre-mixer, maintained at 160-180 degrees Celsius (° C.) and atmospheric pressure. From there, the mixture can flow into a first pre-polymerization vessel where the proportion of DPC to BPA can optionally be increased by adding additional DPC. Optionally, another catalyst stream can be added in the feed stream to the first pre-polymerizer reactor. Temperature and vacuum can be increased (230-260° C., 140-200 millibar absolute (mbara)) and phenol byproduct from polymerization reaction can be removed. The effluent from this first pre-polymerizer can be pumped into a second pre-polymerization reactor where higher temperature (270-290° C.) and deeper vacuums (30-50 mbara) can be applied for further phenol removal.

After second pre-polymerizer vessel, the effluent can be pumped into a first polymerizer where higher temperatures and increased vacuum can be applied (such as 290-315° C. and 1-2.5 mbara, respectively). The effluent from the first polymerizer can then be further polymerized in a second polymerizer (for example at 290-315° C. and 0.5-1.5 mbara). From this last polymerizer, the resulting polymer can be introduced into a finishing extruder where quencher (to deactivate polymerization catalyst), additives, and colors can be added to the molten polycarbonate. After the extruder, and as last step, the resulting product can be pumped through a melt filter (2.5-50 microns mesh size) to remove gels and other impurities from the polymerization process, after which it can be stranded in a die-head, cooled, pelletized, and packaged.

Overall molar ratio is adjusted for producing different polycarbonate grades and this can be accomplished by fixing the molar ratio of diaryl carbonate to dihydroxy monomer reactants fed to the pre-mix tank (10) and changing diaryl carbonate flowrate in stream D. Undesired changes in molar ratio are detectable by changes in the endcap level of the final polycarbonate product, meaning that lag times of several hours will occur between a correction in molar ratio and its effect in the final produced polycarbonate. As used herein, the term "dihydroxy monomer" has the same meaning as the "aromatic dihydroxy compound."

Figure 2:
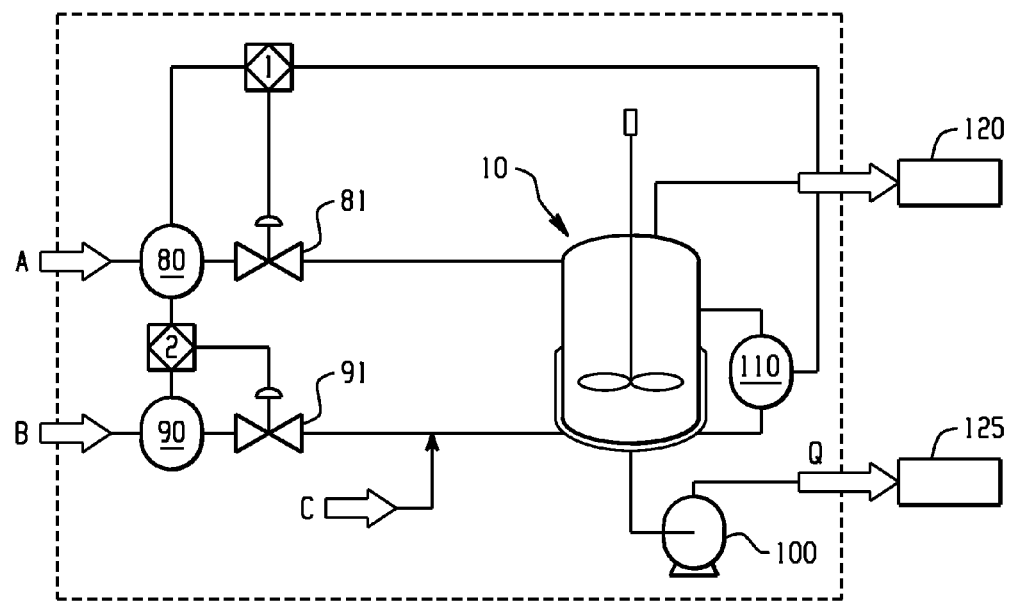
FIG. 2 is a schematic representation of a standard molar ratio control mechanism based on mass-flow meters in a continuous melt polycarbonate plant.

A conventional control scheme for the addition of the diaryl carbonate and the aromatic dihydroxy compound is displayed in FIG. 2. In this control scheme, the level of the mixture comprising a combination of one or more of the aromatic dihydroxy compound (A), diaryl carbonate (B) and catalyst (C) in the pre-mixer (10), is constantly measured by a liquid level transmitter (110). The measured level is read by the control system (1), which then generates a signal to modify the opening of the dihydroxy compound flow control valve (81). The resulting dihydroxy compound flow rate is measured by, for example, a Coriolis mass-flow meter (80). Based on the measured dihydroxy compound flow rate and the target molar ratio of the diaryl carbonate to the aromatic dihydroxy compound, the control system (2) calculates a diaryl carbonate flow rate necessary to maintain the target diaryl carbonate/dihydroxy compound molar ratio. The diaryl carbonate flow meter (90), which measures the diaryl carbonate flow rate, then generates a signal to change the opening of the diaryl carbonate flow control valve (91) to adjust the diaryl carbonate flow rate to the desired level. Catalyst flow (C) is added to the diaryl carbonate stream as specified by process conditions. After mixing, the combination (Q) of the dihydroxy monomer (A), the diaryl carbonate monomer (B) and the catalyst (C) in the pre-mixer (10) are sent to the oligomerization section (125) by using a pump (100). Pre-mixer (10) can be blanketed or vented if needed through a conduit (120).

Figure 3:
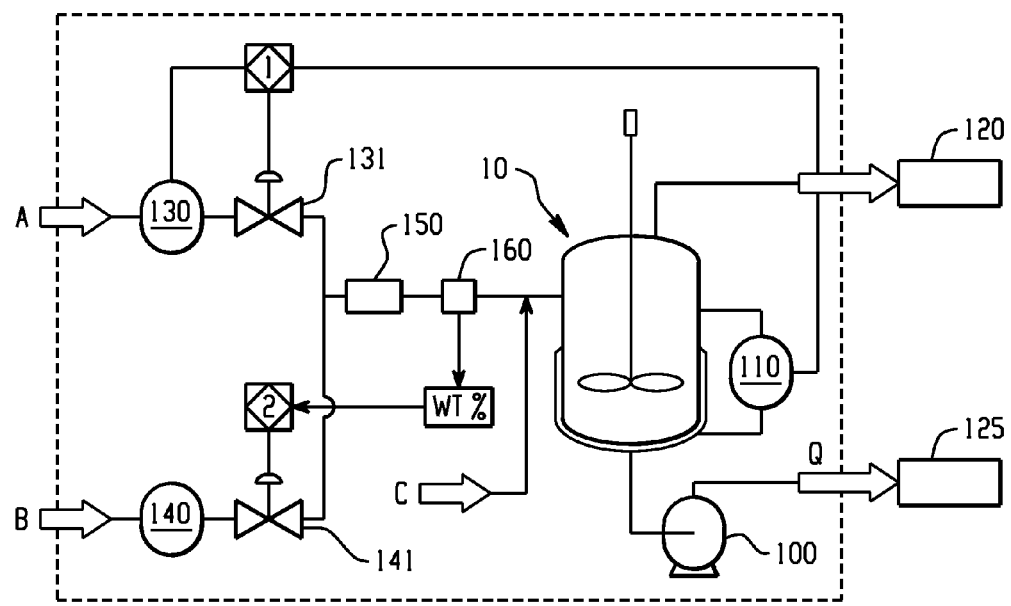
FIG. 3 is a schematic representation of a molar ratio control mechanism based on ultrasound meter in a continuous melt polycarbonate plant.

An improved control scheme is provided by means of an ultrasound device installed as shown in FIG. 3. The sound velocity in the diaryl carbonate/aromatic dihydroxy compound mixture is measured in a process stream comprising the diaryl carbonate and the dihydroxy monomers prior to the addition of the monomers to the pre-mixer. For accuracy, the ultrasound device measures the velocity of sound before any reaction between the diaryl carbonate and the dihydroxy compound takes place to any significant extent, for example, when from 0 to less than 0.1 mol %, less than 0.05 mol %, less than 0.01 mol %, or less than 0.001 mol % of the diaryl carbonate is reacted, and the temperature at which the sound velocity is measured must be fixed at a constant value, for example, within ±1.5° C., within ±1° C., within ±0.5° C., or within ±0.2° C. of the constant value, i.e., the targeted temperature.

As shown in FIG. 3, the dihydroxy monomer (A) and the diaryl carbonate (B) flow streams can be mixed together in, for example, a static mixer (150). Then the combined stream can be analyzed by the ultrasound meter (160) prior to the addition of catalyst (C). The resulting mixture can be added into the monomer pre-mix tank (10). After mixing, the combination (Q) of the dihydroxy monomer (A), the diaryl carbonate monomer (B) and the catalyst (C) in the pre-mixer (10) can be pumped to the oligomerization section (125) through a pump (100). Pre-mixer (10) can be blanketed or vented if needed through a conduit (120).

After measuring the sound velocity by the ultrasound meter, the amounts of the dihydroxy monomer and the diaryl carbonate in the binary mixture of the two monomers can be calculated based on the Equations (1) and (2):

$$\text{Dihydroxy monomer (wt \%)} = a + b \times V_s \quad \text{(Equation 1)}$$

$$\text{Diaryl carbonate monomer (wt \%)} = 100 - (a + b \times V_s) \quad \text{(Equation 2)}$$

wherein $V_s$ (meter/second, m/s) is the sound velocity in the mixture of the dihydroxy monomer and the diaryl carbonate monomer, and "a" and "b" are temperature-dependent constants which can be experimentally determined by measuring the sound velocity in diaryl carbonate and dihydroxy aromatic compound mixtures having known diaryl carbonate to dihydroxy aromatic compound molar or weight ratios at the operating temperature of a process or a step to monitor or control the relative level of a mixture having unknown diaryl carbonate to dihydroxy aromatic compound molar or weight ratio and regressing a linear model, for example, in accordance with Equation 1 or Equation 2. As used herein, the "operating temperature" means the temperature at which a sound velocity is measured. For example, it can refer to the temperature of a process or a step to monitor or control the weight (or molar) percent of a diaryl carbonate or a dihydroxy aromatic compound or the temperature of a process or a step to monitor or control a weight (or molar) ratio of a diaryl carbonate relative to a dihydroxy aromatic compound in a mixture comprising the diaryl carbonate and the dihydroxy aromatic compound.

The weight ratio (WR) or the molar ratio (MR) of the diaryl carbonate monomer relative to the dihydroxy monomer can be calculated by Equations (3) and (4):

$$WR = [100 - (a + b \times Vs)] / (a + b \times Vs) \quad \text{(Equation 3)}$$

$$MR = (Mw1/Mw2) \times [100 - (a + b \times Vs)] / (a + b \times Vs) \quad \text{(Equation 4)}$$

wherein Vs, "a", and "b" are as described in Equations (1) and (2), Mw1 is the molecular weight of the dihydroxy monomer and the Mw2 is the molecular weight of the diaryl carbonate monomer In specific embodiments where the dihydroxy monomer is bisphenol A and the diaryl carbonate is diphenyl carbonate, the molar ratio of diphenyl carbonate relative to bisphenol A can be calculated by Equation 4a:

$$MR = 1.0657 \times [100 - (a + b \times Vs)] / (a + b \times Vs) \quad \text{(Equation 4a)}$$

In an exemplary process, in this control scheme, the level of the mixture comprising the combination of the aromatic dihydroxy compound (A), diaryl carbonate (B) and catalyst (C) in the pre-mixer (10), is constantly measured by a liquid level transmitter (110). The measured level is read by the control system (1), which generates a signal to modify the opening of the dihydroxy monomer flow control valve (131). The diaryl carbonate flow rate required to maintain the specified diaryl carbonate to dihydroxy monomer molar ratio, is adjusted by the control system (2) by changing the opening of the diaryl carbonate flow control valve (141), so the diaryl carbonate/dihydroxy compound molar ratio calculated via the measurement of the sound velocity of the mixture, coincides with the target value. Flowmeters 130 and 140 for dihydroxy compound (A) and diaryl carbonate (B) respectively, are not required in this control scheme but can be optionally employed to measure and indicate the actual flow rates and therefore the throughput of the plant.

After polymerization, the polycarbonate can be extruded and optionally filtered to form a polycarbonate composition. The polycarbonate composition can comprise another polymer(s), for example another, different, polycarbonate, a polyester, a polysiloxane, additives (e.g., an impact modifier(s), stabilizer(s), colorant(s), flame retardant(s), etc.), or one or more of the foregoing to form a polycarbonate blend.

The additive can include various additives, with the proviso that the additive(s) are selected so as to not significantly adversely affect the desired properties of the thermoplastic composition. Such additives can be mixed at a suitable time during the mixing of the components for forming the composition. The additive can include impact modifiers, fillers, reinforcing agents, antioxidants, heat stabilizers, light stabilizers, ultraviolet (UV) light stabilizers, plasticizers, lubricants, mold release agents, antistatic agents, colorants such as such as titanium dioxide, carbon black, and organic dyes, surface effect additives, radiation stabilizers, flame retardants, anti-drip agents, or combinations comprising one or more of the foregoing. The total amount of additives (other than any impact modifier, filler, or reinforcing agents) can be 0.01 to 5 weight %, based on the total weight of the composition.

The impact modifier can include natural rubber, fluoroelastomers, ethylene-propylene rubber (EPR), ethylene-butene rubber, ethylene-propylene-diene monomer rubber (EPDM), acrylate rubbers, hydrogenated nitrile rubber (HNBR) silicone elastomers, and elastomer-modified graft copolymers such as styrene-butadiene-styrene (SBS), styrene-butadiene rubber (SBR), styrene-ethylene-butadiene-styrene (SEBS), acrylonitrile-butadiene-styrene (ABS), acrylonitrile-ethylene-propylene-diene-styrene (AES), styrene-isoprene-styrene (SIS), methyl methacrylate-butadiene-styrene (MBS), high rubber graft (HRG), or a combination comprising one or more of the foregoing. The thermoplastic composition can be essentially free of chlorine and bromine Essentially free of chlorine and bromine refers to materials produced without the intentional addition of chlorine or bromine or chlorine or bromine containing materials. It is understood however that in facilities that process multiple products, a certain amount of cross contamination can occur resulting in bromine and/or chlorine levels typically on the parts per million by weight scale. With this understanding it can be readily appreciated that essentially free of bromine and chlorine can be defined as having a bromine and/or chlorine content of less than or equal to 100 parts per million by weight (ppm), less than or equal to 75 ppm, or less than or equal to 50 ppm. When this definition is applied to the fire retardant, it is based on the total weight of the fire retardant. When this definition is applied to the thermoplastic composition, it is based on the total weight of the composition, excluding any filler.

Transparent compositions can be produced by manipulation of the process used to manufacture the polycarbonate composition. One example of such a process to produce transparent polycarbonate compositions is described in U.S. Patent Application No. 2003/0032725.

Applicant found that deviations in the monomer molar ratio could be greatly reduced by using ultrasound meters to control the molar ratio of the diaryl carbonate and the aromatic dihydroxy compound. For example, the standard of derivation can be equal to or less than 0.02, equal to or less than 0.01, equal to or less than 0.005, or equal to or less than 0.002. As a result, the polycarbonate prepared according to the process of this disclosure has controlled endcap ratios. As used herein, the endcap ratio is the molar ratio between the phenyl carbonate chain end-groups to the total amount of end-groups, which is the sum of phenyl carbonate plus hydroxyl moieties.

Control of the monomer molar ratio as described herein, and thus the endcap ratios allows manufacture of polycarbonates with desired properties. For example, control of the endcap ratios allows manufacture of polycarbonates with excellent optical properties and stable heat aging properties, which can be used in lenses, building and construction and electronic applications, where thermal stability, clarity, and transparency are desirable properties. An example of a heat aging property is yellowing upon aging. As shown in the Examples, an article made from a composition comprising the polycarbonate product can have a delta yellowness index (deltaYI) of less than 5 units, or less than 4 units, or less than 3 units, after the article is exposed to a temperature of 130° C. for a specified time, e.g., 250 hours, 500 hours, 750 hours, 800 hours, or 1000 hours. An article made from a composition comprising the polycarbonate product can have a delta yellowness index less than 4 units, or less than 3 units, or less than 2 units or less than 1 unit after the article is exposed to a temperature of 130° C. for a specified time, e.g., 200 hours, 250 hours, 500 hours, or 750 hours. An article made from a composition comprising the polycarbonate product can have a delta yellowness index less than 2 units or less than 1 unit after the article is exposed to a temperature of 130° C. for a specified time, e.g., 200 hours, 250 hours, or 500 hours. As used herein, the delta YI refers to the yellowness index difference of the article before and after the aging. The yellowness index can be measured using an XRite Color i7 spectrophotometer.

The following examples are merely illustrative and are not intended to limit devices made in accordance with the disclosure to the materials, conditions, or process parameters set forth therein.

EXAMPLES

Experiments were run in a continuous melt polycarbonate plant, a schematic of which is shown in FIG. 1. In the experiments, 39.8 kilograms per hour (kg/h) Bisphenol-A (BPA) and 37.3 kg/h of diphenylcarbonate (DPC), molar ratio of DPC to BPA=1.0 were fed into a continuously stirred vessel (formulation tank). The formulation tank was operated at atmospheric pressure and 170° C. A 3.2 wt % aqueous solution of an onium type/beta catalyst (e.g. tetrabutyl phosphonium acetate) was also added to the vessel at a rate of 83 milliliter per hour (ml/h), providing an equilibrated mixture of unreacted monomers, phenol and low molecular oligomers.

Additional DPC (1.67 kg/h) and an alpha catalyst (1.3 milliliter per minute (ml/min) of an aqueous solution of 50 ppm of NaKHPO$_4$) were added to the outlet stream of the formulation tank and then pumped to a continuously stirred reactor (first pre-polymerizer), which was operated at 257° C. and 180 mbar vacuum so that reaction byproduct, phenol, was removed and thus reaction progressed. The vapor phase containing phenol and unreacted monomers BPA and DPC was continuously distilled in a scrubber where reflux ratio was adjusted so that the column head temperature was 127° C. to yield high purity phenol and thus recovering the unreacted BPA and DPC back into the first pre-polymerizer.

The outlet stream of the first pre-polymerizer was then pumped to a second pre-polymerizer where 280° C. and 37 mbar vacuum were applied to further displace the reaction equilibrium and drive the reaction forward. The effluent of this second pre-polymerizer was conveyed to the forthcoming polymerization section where two horizontal polymerization reactors connected in series were used to reach the final viscosity target.

The first horizontal polymerization reactor operated at 300° C. and 2.5 to 3.0 mbar vacuum. Phenol was removed due to the process conditions applied and the reaction mixture therein was continuously agitated by an agitator. The polymer stream exiting the first polymerizer was then pumped to the second polymerizer where a deeper (1.0 to 1.5 mbar) vacuum was set to further build polycarbonate viscosity.

The product polycarbonate exiting the second polymerizer was then optionally introduced to a six-barrel twin-screw extruder 411 to mix polymer with additives for specific applications. Polycarbonate exiting the extruder was filtered and pelletized.

Comparative Example 1

DPC and BPA in molten state were fed to a continuous polycarbonate production plant as per FIG. 1 and above description. Molar ratio of 1.000 was set up in the control system based on mass-flow meters and flow rates of both DPC and BPA were adjusted and controlled as per FIG. 2.

Figure 4:
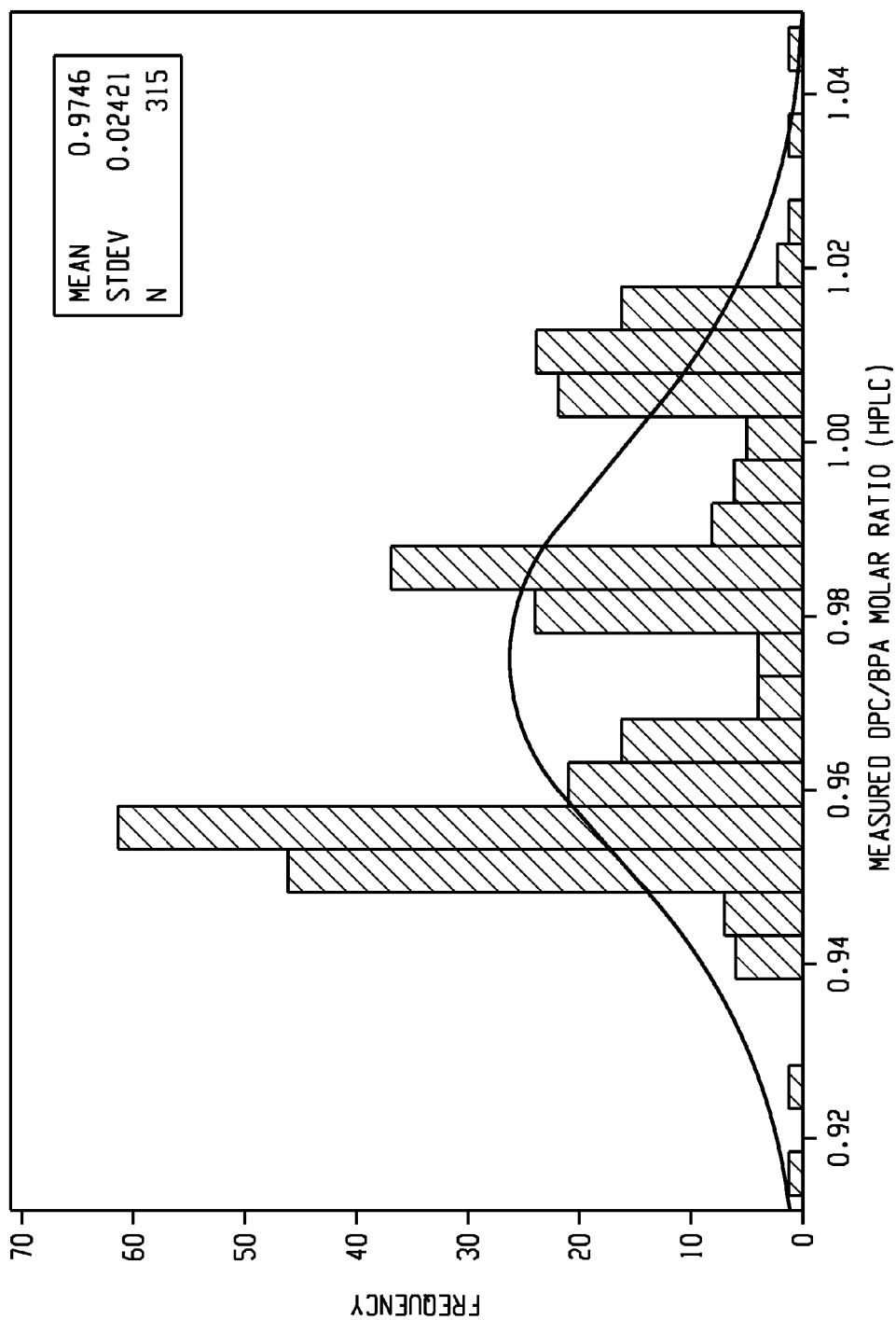
FIG. 4 shows measured molar ratio of DPC to BPA in the pre-mixer versus frequency in a continuous melt polycarbonate plant wherein the molar ratio is controlled by mass-flow meters.

The plant was operated according to this control philosophy and the molar ratio in monomer pre-mixer (formulation tank) was analyzed by high pressure liquid chromatography (HPLC) in the laboratory and compared with the theoretical value. The measured molar ratio of DPC to BPA in the pre-mixer versus frequency is shown in FIG. 4. The molar ratio analyzed along 315 samples presented a mean of 0.9746 and a standard deviation of 0.0242.

The effect of a change in DPC/BPA overall molar ratio on the endcap ratio of the polycarbonate product was then studied. While keeping all other process parameters constant, changes in the endcap level of the resultant polycarbonate based on the overall DPC/BPA molar ratio (sum of DPC moles added in streams B+D/moles of BPA added by stream A) were determined and the results are shown if FIGS. 5a and 5b. The relationship between endcap and formulated molar ratio is approximately 0.920% endcap points per each 0.001 change in molar ratio and this relationship should be valid only for the regular interval of endcap values, this is 60-90%. For values other than these, non-linear effects have important influence and this relationship is not valid.

The effect of a change in DPC/BPA molar ratio on molecular weight of the polycarbonate was also determined from FIGS. 5a and 5b. As shown in these figures, an increase of the DPC/BPA molar ratio reduces the molecular weight, whereas a decrease of the DPC/BPA molar ratio increases the molecular weight.

FIG. 6 represents the heat aging properties of the produced polycarbonates, to illustrate the effect that different endcap levels have on product properties and particularly on product performance. In FIG. 6, several polycarbonate samples were prepared in a continuous melt polymerization plant wherein the process is illustrated in FIG. 1. Two different targeted endcap levels, 70% and 80%, were produced by changing the molar ratio in the pre-mix tank (Melt PC, Endcap about 70% and Melt PC, Endcap about 80%). The rest of the process conditions were kept constant. Molten polymer from the second polymerizer was added with 3,000 ppm of polyethylene terephthalate (PETS), 360 ppm of tris(2,4-di-(tert)-butylphenyl)phosphite (Irgafos* 168), 200 ppm of octadecyl 3-(3,5-di-tert-butyl-4-hydroxyphenyl)propionate (Irganox* 1076), 3,000 ppm of 2-(2-hydroxy-5-octylphenyl)-benzotriazole (UV5411*) and 2 ppm of butyl tosylate as quencher.

Next, 4 mm color plaques were molded form these materials and introduced in an oven at 130° C. After certain time period (between 200 and 1000 hours), plaques were removed from oven and yellowness index (YI) measured vs. reference starting material using an XRite Color i7 spectrophotometer.

Also for comparison, an interfacial polycarbonate with 100% phenol endcap (IF PC, endcap about 100%) and with the same additives (except the butyl tosylate quencher) was tested following the same procedure.

As shown in FIG. 6, lower endcap level produces polycarbonate having higher yellowness index after exposure to thermal oxidation conditions (heat aging). Control of the endcap level therefore allows control of heat aging properties. The color stability during thermal oxidation is important for polycarbonate as this product is sought after for its clarity, clear color, and transparency in lenses, building and construction and electronic applications.

Example 2

DPC and BPA in molten state were fed to a continuous polycarbonate production plant as per FIG. 1 and above description. A molar ratio of 1.000 was set up in the control system and flow rates of both DPC and BPA were adjusted and controlled as per FIG. 3. Both molten monomers were fed into a static mixer operated at a constant temperature of 170±0.2° C. An ultrasound detector (model LiquiSonic* from SensoTech GmbH) was used to measure sound velocity in the DPC/BPA mixture and to determine the composition (weight percent of DPC and BPA as well as their molar ratio).

Figure 7:
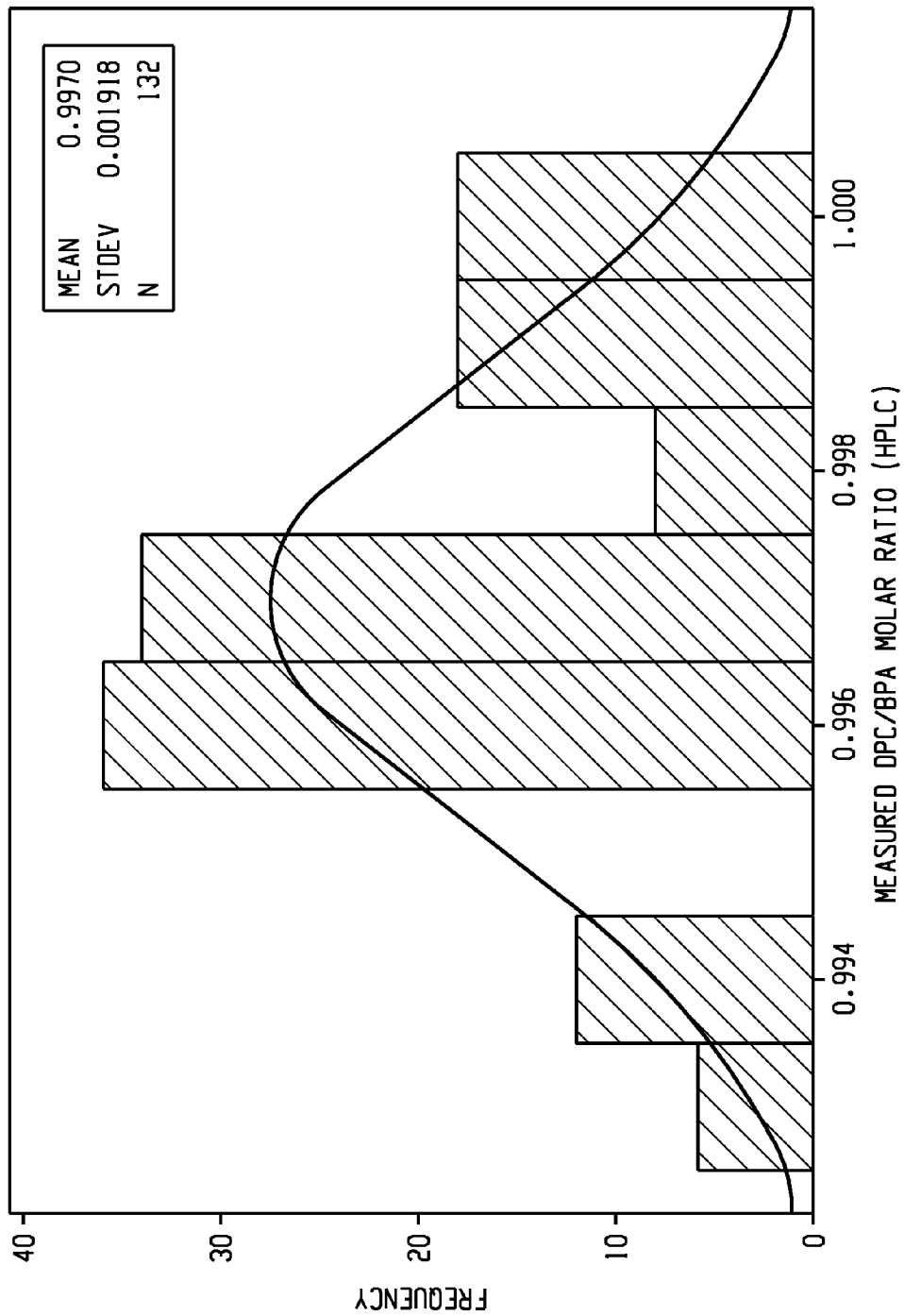
FIG. 7 shows measured molar ratio of DPC to BPA in the pre-mixer versus frequency in a melt polycarbonate plant wherein the molar ratio is controlled by an ultrasound meter.

The plant was operated according to this control philosophy and molar ratio in monomer mix (formulation tank) was analyzed by HPLC in the laboratory and compared with theoretical value. The results are shown in FIG. 7.

The molar ratio analyzed along 134 samples presented a mean of 0.9970 and a standard deviation of 0.0019. This is an order of magnitude more precise and far more accurate than the standard method based on Coriolis mass flow meters as shown in comparative example 1. Not being bound by any theory, the DPC/BPA molar ratio or vice versa is critical to end-cap and molecular weight of the polycarbonate manufactured from DPC and BPA, and therefore a more precise analysis of molar ratio provides better control of end-product quality, for example, the molecular weight, the endcap ratio and heat stability.

In a first embodiment, a process for monitoring a relative level of an aromatic dihydroxy compound or a diaryl carbonate in a mixture comprising the aromatic dihydroxy compound and the diaryl carbonate comprises: measuring a sound velocity, $V_s$, in the mixture at an operating temperature of the process; and determining the relative level of the aromatic dihydroxy compound or the diaryl carbonate in the mixture based on Equation 1, 2, 3 or 4:

$$WP1 = a + b \times V_s \quad \text{(Equation 1)}$$

$$WP2 = 100 - (a + b \times V_s) \quad \text{(Equation 2)}$$

$$WR = [100 - (a + b \times V_s)]/(a + b \times V_s) \quad \text{(Equation 3) or}$$

$$MR = (Mw1/Mw2) \times [100 - (a + b \times V_s)]/(a + b \times V_s) \quad \text{(Equation 4)}$$

wherein WP1 is the weight percent of the aromatic dihydroxy compound in the mixture, WP2 is the weight percent of the diaryl carbonate in the mixture, Mw1 is the molecular weight of the aromatic dihydroxy compound, Mw2 is the molecular weight of the diaryl carbonate, WR is the weight ratio of the diaryl carbonate to the aromatic dihydroxy compound, MR is the molar ratio of the diaryl carbonate to the aromatic dihydroxy compound, and a and b are constants as described above. The process can further comprise calculating the weight ratio WR or molar ratio MR of the diaryl carbonate to the aromatic dihydroxy compound; comparing the calculated weight ratio WR or molar ratio MR to a desired weight ratio or molar ratio of the diaryl carbonate to the aromatic dihydroxy compound; and if needed, adjusting the amount of the aromatic dihydroxy compound or the amount of the diaryl carbonate added to the mixture to achieve the desired ratio, optionally wherein the standard deviation of the calculated weight ratio WR or molar ratio MR to a desired weight ratio or molar ratio is less than 0.02, less than 0.01, less than 0.005, less than 0.001, or less than 0.0005, for example the standard deviation can be 0.0001 to less than 0.02, or 0.0001 to less than 0.01, or 0.0001 to less than 0.005, or 0.0001 to less than 0.001.

In a second embodiment, a continuous process for the manufacture of a polycarbonate comprises: combining an aromatic dihydroxy compound stream and a diaryl carbonate stream to form a mixture; controlling a weight or molar ratio of the diaryl carbonate to the aromatic dihydroxy compound by: measuring a sound velocity, $V_s$, in the mixture at an operating temperature of the controlling step; and determining the weight or molar ratio of the diaryl carbonate to the aromatic dihydroxy compound in the mixture based on Equation 3 or Equation 4: $WR = [100 - (a + b \times V_s)]/(a + b \times V_s)$ (Equation 3); $MR = (Mw1/Mw2) \times [100 - (a + b \times V_s)]/(a + b \times V_s)$ (Equation 4); wherein WR is the weight ratio of the diaryl carbonate to the aromatic dihydroxy compound, MR is the molar ratio of the diaryl carbonate to the aromatic dihydroxy compound, Mw1 is the molecular weight of the aromatic dihydroxy compound, Mw2 is the molecular weight of the diaryl carbonate, and a and b are constants; and adjusting a flow rate of at least one of the aromatic dihydroxy compound stream and the diaryl carbonate stream, if needed, to achieve a desired weight or molar ratio of the diaryl carbonate to the aromatic dihydroxy compound; and polymerizing the aromatic dihydroxy compound and the diaryl carbonate in the presence of a catalyst to produce the polycarbonate, optionally wherein the standard deviation of the calculated weight ratio WR or molar ratio MR to a desired weight ratio or molar ratio is less than 0.02, less than 0.01, less than 0.005, less than 0.001, or less than 0.0005, for example the standard deviation can be 0.0001 to less than 0.02, or 0.0001 to less than 0.01, or 0.0001 to less than 0.005, or 0.0001 to less than 0.001.

In the second embodiment, (i) the process further comprises adding a catalyst stream to the mixture, and adding the mixture to a monomer pre-mixer; and/or (ii) adjusting the flow rate comprises adjusting the opening of a valve controlling the flow of at least one of the aromatic dihydroxy compound stream and the diaryl carbonate stream.

In any of the above embodiments, (i) the process further comprises mixing the mixture before determining the sound velocity; (ii) the mixture is a binary mixture of the aromatic dihydroxy compound and the diaryl carbonate; (iii) the sound velocity in the mixture is measured through an ultrasound meter; (iv) a and b are temperature-dependent constants; and wherein a and b are determined by measuring the sound velocity in diaryl carbonate and dihydroxy aromatic compound mixtures having known diaryl carbonate and dihydroxy aromatic molar or weight ratios at the operating temperature and regressing a linear model; (v) the sound velocity is measured before any substantial reaction between the aromatic dihydroxy compound and the diaryl carbonate takes place; (vi) the aromatic dihydroxy compound is bisphenol A, and the diaryl carbonate is diphenyl carbonate; or (vii) the operating temperature is fixed within ±1° C. of a constant value.

A polycarbonate manufactured by the process is provided. For example, when the standard deviation of the calculated weight ratio WR or molar ratio MR to a desired weight ratio or molar ratio is less than 0.02, less than 0.01, less than 0.005, less than 0.001, or less than 0.0005, or the standard deviation is 0.0001 to less than 0.02, or 0.0001 to less than 0.01, or 0.0001 to less than 0.005, or 0.0001 to less than 0.001, an article made from a composition comprising the manufactured polycarbonate has a delta yellowness index of less than 5 units after the article is exposed to a temperature of 130° C. for 800 hours. Alternatively, or in addition, the article can have a delta yellowness index of less than 2 units after the article is exposed to a temperature of 130° C. for 200 hours.

All ranges disclosed herein are inclusive of the endpoints, and the endpoints are independently combinable with each other (e.g., ranges of "up to 25 wt % or, more specifically, 5 wt % to 20 wt %", is inclusive of the endpoints and all intermediate values of the ranges of "5 wt % to 25 wt %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The term "or"

means "and/or." The term "and/or" includes any and all combinations of one or more of the associated listed items. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications, variations, improvements, and substantial equivalents.

What is claimed is:

1. A process for monitoring a relative level of an aromatic dihydroxy compound or a diaryl carbonate in a mixture comprising the aromatic dihydroxy compound and the diaryl carbonate, the process comprising:
    measuring a sound velocity, Vs, in the mixture at an operating temperature of the process; and
    determining the relative level of the aromatic dihydroxy compound or the diaryl carbonate in the mixture based on Equation 1, 2, 3 or 4:

$$WP1 = a + b \times Vs \quad \text{(Equation 1)}$$

$$WP2 = 100 - (a + b \times Vs) \quad \text{(Equation 2)}$$

$$WR = [100 - (a + b \times Vs)]/(a + b \times Vs) \quad \text{(Equation 3)}$$

$$MR = (Mw1/Mw2) \times [100 - (a + b \times Vs)]/(a + b \times Vs) \quad \text{(Equation 4)}$$

wherein
WP1 is the weight percent of the aromatic dihydroxy compound in the mixture,
WP2 is the weight percent of the diaryl carbonate in the mixture,
Mw1 is the molecular weight of the aromatic dihydroxy compound,
Mw2 is the molecular weight of the diaryl carbonate,
WR is the weight ratio of the diaryl carbonate to the aromatic dihydroxy compound,
MR is the molar ratio of the diaryl carbonate to the aromatic dihydroxy compound, and a and b are constants.

2. The process of claim 1, further comprising:
    calculating the weight ratio WR or molar ratio MR of the diaryl carbonate to the aromatic dihydroxy compound;
        comparing the calculated weight ratio WR or molar ratio MR to a desired weight ratio or molar ratio of the diaryl carbonate to the aromatic dihydroxy compound; and
        if needed, adjusting the amount of the aromatic dihydroxy compound or the amount of the diaryl carbonate added to the mixture to achieve the desired weight ratio WR or molar ratio MR.

3. The process of claim 1, further comprising mixing the mixture before determining the sound velocity.

4. The process of claim 1, wherein the mixture is a binary mixture of the aromatic dihydroxy compound and the diaryl carbonate.

5. The process of claim 1, wherein the sound velocity in the mixture is measured through an ultrasound meter.

6. The process of claim 1, wherein a and b are temperature-dependent constants; and wherein a and b are determined by measuring the sound velocity in diaryl carbonate and dihydroxy aromatic compound mixtures having known diaryl carbonate and dihydroxy aromatic molar or weight ratio at the operating temperature and regressing a linear model.

7. The process of claim 1, wherein the sound velocity is measured before any substantial reaction between the aromatic dihydroxy compound and the diaryl carbonate takes place.

8. The process of claim 1, wherein the aromatic dihydroxy compound is bisphenol A, and the diaryl carbonate is diphenyl carbonate.

9. The process of claim 1, wherein the operating operation temperature is fixed within ±1° C. of a constant value.

10. A continuous process for the manufacture of a polycarbonate comprising:
    combining an aromatic dihydroxy compound stream and a diaryl carbonate stream to form a mixture;
    controlling a weight or molar ratio of the diaryl carbonate to the aromatic dihydroxy compound by:
        measuring a sound velocity, Vs, in the mixture at an operating temperature of the controlling step; and
        determining the weight or molar ratio of the diaryl carbonate to the aromatic dihydroxy compound in the mixture based on Equation 3 or Equation 4:

$$WR = [100 - (a + b \times Vs)]/(a + b \times Vs) \quad \text{(Equation 3)}$$

$$MR = (Mw1/Mw2) \times [100 - (a + b \times Vs)]/(a + b \times Vs) \quad \text{(Equation 4)}$$

wherein Mw1 is the molecular weight of the aromatic dihydroxy compound, Mw2 is the molecular weight of the diaryl carbonate, WR is the weight ratio of the diaryl carbonate to the aromatic dihydroxy compound, MR is the molar ratio of the diaryl carbonate to the aromatic dihydroxy compound, and a and b are constants; and
    adjusting a flow rate of at least one of the aromatic dihydroxy compound stream and the diaryl carbonate stream, if needed, to achieve a desired weight or molar ratio of the diaryl carbonate to the aromatic dihydroxy compound; and
    polymerizing the aromatic dihydroxy compound and the diaryl carbonate in the presence of a catalyst to produce the polycarbonate.

11. The process of claim 10, further comprising adding a catalyst stream to the mixture, and adding the mixture to a monomer pre-mixer.

12. The process of claim 10, wherein adjusting the flow rate comprises adjusting opening of a valve controlling the flow of at least one of the diaryl carbonate and the aromatic dihydroxy compound.

13. A polycarbonate manufactured by the process of claim 10.

14. The polycarbonate of claim 13, wherein the standard deviation of a determined weight ratio WR or molar ratio MR to a desired weight ratio or molar ratio is less than 0.02; and
    an article made from the polycarbonate has a delta yellowness index of less than 5 units after the article is exposed to a temperature of 130° C. for 800 hours.

15. The polycarbonate of claim 14, wherein an article made from the polycarbonate has a delta yellowness index of less than 2 units after the article is exposed to a temperature of 130° C. for 200 hours.

16. The process of claim 10, wherein the standard deviation of a determined weight ratio WR or molar ratio MR to a desired weight ratio or molar ratio is less than 0.005.

17. A process for monitoring a relative level of an aromatic dihydroxy compound or a diaryl carbonate in a mixture comprising the aromatic dihydroxy compound and the diaryl carbonate, the process comprising:
   measuring a sound velocity, Vs, in the mixture at an operating temperature of the process; and
   determining the relative level of the aromatic dihydroxy compound or the diaryl carbonate in the mixture based on Equation 1, 2, 3 or 4:

$WP1 = a + b \times Vs$ (Equation 1)

$WP2 = 100 - (a + b \times Vs)$ (Equation 2)

$WR = [100 - (a + b \times Vs)]/(a + b \times Vs)$ (Equation 3)

$MR = (Mw1/Mw2) \times [100 - (a + b \times Vs)]/(a + b \times Vs)$ (Equation 4)

wherein
WP1 is the weight percent of the aromatic dihydroxy compound in the mixture,
WP2 is the weight percent of the diaryl carbonate in the mixture,
Mw1 is the molecular weight of the aromatic dihydroxy compound,
Mw2 is the molecular weight of the diaryl carbonate,
WR is the weight ratio of the diaryl carbonate to the aromatic dihydroxy compound,
MR is the molar ratio of the diaryl carbonate to the aromatic dihydroxy compound, and
a and b are constants, further comprising:
   calculating the weight ratio WR or molar ratio MR of the diaryl carbonate to the aromatic dihydroxy compound;
   comparing the calculated weight ratio WR or molar ratio MR to a desired weight ratio or molar ratio of the diaryl carbonate to the aromatic dihydroxy compound; and
   if needed, adjusting the amount of the aromatic dihydroxy compound or the amount of the diaryl carbonate added to the mixture to achieve the desired weight ratio WR or molar ratio MR, wherein the standard deviation of a calculated weight ratio WR or molar ratio MR to a desired weight ratio or molar ratio is less than 0.02.

18. The process of claim 17, wherein the standard deviation of a calculated weight ratio WR or molar ratio MR to a desired weight ratio or molar ratio is less than 0.005.

19. The polycarbonate of claim 13, wherein the standard deviation of a determined weight ratio WR or molar ratio MR to a desired weight ratio or molar ratio is less than 0.005.

* * * * *